United States Patent [19]
Brieaddy et al.

[11] Patent Number: 5,817,652
[45] Date of Patent: Oct. 6, 1998

[54] HYPOLIPIDAEMIC CONDENSED 1,4-THIAZEPINES

[75] Inventors: Lawrence Edward Brieaddy, Raleigh; Gordon Lewis Hodgson, Jr., Durham, both of N.C.

[73] Assignee: Glaxo Wellcome Inc., Reasearch Triangle park, N.C.

[21] Appl. No.: 505,232

[22] PCT Filed: Feb. 15, 1994

[86] PCT No.: PCT/GB94/00299

§ 371 Date: Aug. 15, 1995

§ 102(e) Date: Aug. 15, 1995

[87] PCT Pub. No.: WO94/18183

PCT Pub. Date: Aug. 18, 1994

[30] Foreign Application Priority Data

Feb. 15, 1993 [GB] United Kingdom ............... 90303014
Jul. 22, 1993 [GB] United Kingdom ............... 9315154

[51] Int. Cl.⁶ .......................... C07D 28/10; A61K 31/55
[52] U.S. Cl. ................................ 514/211; 540/552
[58] Field of Search ................. 540/552; 514/211

[56] References Cited

U.S. PATENT DOCUMENTS

| | | | |
|---|---|---|---|
| 3,362,962 | 1/1968 | Reeder et al. | 540/548 |
| 3,503,985 | 3/1970 | Reeder et al. | |
| 3,523,974 | 8/1970 | Reeder et al. | |
| 3,530,139 | 9/1970 | Reeder et al. | |
| 3,631,089 | 12/1971 | Reeder et al. | |
| 5,276,025 | 1/1994 | Baldwin et al. | 514/211 |

FOREIGN PATENT DOCUMENTS

93/16055  8/1993  WIPO .

OTHER PUBLICATIONS

Sternbach et al., "A New Type of 1,4–Benzothiazepine Derivatives," J. Org. Chem., 30(8), 2812–2818 (1965).
Nair et al., "Synthesis & Reactions of Benz[I,4]thiazepines Derivatives," Indian J. Chem., 7(9), 862–865 (1969).
Grundy, "Cholesterol and Coronary Heart Disease," J. Amer. Med. Assn., 256(20), 2849–2859 (1986).
Sugano et al., ".Supression of Atherosclerosis in Cholesterol–Fed Rabbits by Diltiazem Injection,"Arteriosclerosis, 6(2), 237–241 (1986).
"Pharmaceutical Compounds," Research Disclosure 35450, 691–693 (Oct. 1993).
Szabo et al., "Synthesis and Spectroscopic Investigation of 1,4–Benzothiazepine Derivatives," Chemical Abstracts 108:221680x (1988).
Szabo et al., "Saturated Heterocycles. Part 116. Synthesis and Spectroscopic Investigations of 1,4–Benxothiazepine Derivatives," Heterocycles, 108:5984g (1988).

*Primary Examiner*—John M. Ford
*Attorney, Agent, or Firm*—Robert T. Hrubiec

[57] ABSTRACT

The invention provides a compound of formula (I), wherein n is an integer of from 0 to 2; R is an optional substituent; $R^1$ is hydrogen or $C_{1-6}$alkyl; $R^2$ is an atom or group selected from hydrogen, $C_{1-4}$alkyl (including cycloalkyl and cycloalkylalkyl), $C_{1-4}$alkoxy, pyrryl, thienyl, pyridyl, 1,3-benzodioxolo, phenyl and naphthyl, which groups are optionally substituted; $R^3$ is hydrogen, OH, $C_{1-6}$alkyl, $C_{1-6}$alkoxy or —O $C_{1-6}$acyl; $R^4$ is a group independently selected from $C_{1-6}$alkyl (including cycloalkyl and cycloalkylalkyl), $C_{2-6}$alkenyl, and $C_{2-6}$-alkynyl which groups are optionally substituted; $R^5$ is a group independently selected from $C_{2-6}$alkyl (including cycloalkyl and cycloalkylalkyl), $C_{2-6}$alkenyl and $C_{2-6}$alkynyl, which groups are optionally substituted; or $R^4$ and $R^5$, together with the carbon atom to which they are attached, form a $C_{3-7}$spiro cycloalkyl group which is optionally substituted; $R^6$ and $R^7$ are independently selected from hydrogen and $C_{1-6}$alkyl; and X is an aromatic or non-aromatic monocyclic or bicyclic ring system having from 5 to 10 carbon atoms (including the two carbon atoms forming part of the thiazepine ring) wherein optionally one or more of the carbon atoms is/are replaced by heteroatom(s) independently selected from nitrogen, oxygen and sulphur, or X is an aromatic or non-aromatic monocyclic or bicyclic ring system having from 5 to 10 carbon atoms (including the two carbon atoms forming part of the thiazepine ring) wherein one or more of the carbon atoms is/are replaced by heteroatom(s) independently selected from nitrogen, oxygen and sulphur; and salts, solvates and physiologically functional derivatives thereof, pharmaceutical formulations comprising such compounds, processes for their preparation and their use in reducing bile acid uptake and hence as hypolipidaemic compounds.

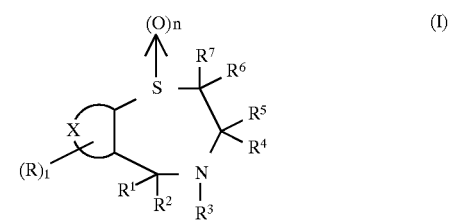

9 Claims, No Drawings

HYPOLIPIDAEMIC CONDENSED 1,4-THIAZEPINES

This is a 371 of PCT/GB94/00299, filed Feb. 15, 1994.

The present invention is concerned with new hypolipidaemic compounds, with processes and novel intermediates for their preparation, with pharmaceutical compositions containing them and with their use in medicine, particularly in the prophylaxis and treatment of hypolipidaemic conditions, such as atherosclerosis.

Hypolipidamic conditions are often associated with elevated plasma concentrations of low density lipoprotein (LDL) cholesterol and very low density lipoprotein (VLDL) cholesterol. Such concentrations may be reduced by decreasing the absorption of bile acids from the intestine. One method by which this may be achieved is to inhibit the bile acid active uptake system in the terminal ileum. Such inhibition stimulates the conversion of cholesterol to bile acid by the liver and the resulting increase in demand for cholesterol produces a corresponding increase in the rate of clearance of LDL and VLDL cholesterol from the blood plasma or serum.

There has now been identified a novel class of heterocyclic compounds which reduce the plasma or serum concentrations of LDL and VLDL cholesterol and in consequence are particularly useful as hypolipidaemic agents. By decreasing the concentrations of cholesterol and cholesterol ester in the plasma, the compounds of the present invention retard the build-up of atherosclerotic lesions and reduce the incidence of coronary heart disease-related events. The latter are defined as cardiac events associated with increased concentrations of cholesterol and cholesterol ester in the plasma or serum.

For the purposes of this specification, a hyperlipidaemic condition is defined as any condition wherein the total cholesterol concentration (LDL+VLDL) in the plasma or serum is greater than 240 mg/dL (6.21 mmol/L) (J. Amer. Med. Assn. 256, 20, 2849–2858(1986)). U.S. Pat. No. 3,362,962 describes a genus of benzothiazepines outside the scope of the present invention which have muscle-relaxant and anticonvulsant activity; there is no disclosure in the patent specification that the compounds described therein may be useful as hypolipidaemic agents.

According to the present invention, there is provided a compound of formula (I)

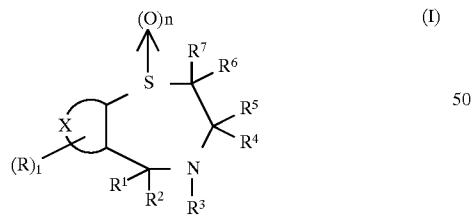

(I)

l is an integer of from 0 to 4;
n is an integer of from 0 to 2;
R is an atom or group selected from halogen, cyano, nitro, alkyl, alkoxy, aryl, heteroaryl, aryloxy, arylalkoxy, aralkyl, alkaryl, $-O(CH_2)_pSO_3R^{11}$, $-O(CH_2)_pNR^{11}R^{12}$, $-O(CH_2)_pN^+R^{11}R^{12}R^{14}$, $-COR^{11}$, $-CO_2R^{11}$, $-CONR^{11}R^{12}$, $-CH_2OR^{11}$, $-NR^{11}R^{12}$, $-NHCOR^{11}$, $-NHSO_2R^{11}$, $-SR^{11}$, $-SO_2R^{11}$, $-SO_2NR^{11}R^{12}$, $-SO_3R^{11}$ wherein p is an integer of from 1 to 4, $R^{11}$ and $R^{12}$ are independently selected from hydrogen, $C_{1-6}$ alkyl and phenyl, and $R^{14}$ is hydrogen or $C_{1-6}$ alkyl or R is a group $-OCH_2O-$ which forms a further ring attached to X, wherein said alkyl, alkoxy, aryl, heteroaryl, aryloxy, arylalkoxy, aralyl and alkaryl groups are optionally substituted by one or more atoms or groups selected from halogen, nitro, nitrile, alkyl, alkoxy, $-COR^{11}$, $-CO_2R^{11}$, $-SO_3R^{11}$ wherein $R^{11}$ is as hereinbefore defined and $-NR^{14}R^{15}$ wherein $R^{14}$ is as hereinbefore defined and $R^{15}$ is hydrogen or $C_{1-6}$ alkyl;

$R^1$ is hydrogen or $C_{1-6}$ alkyl;

$R^2$ is an atom or group selected from hydrogen, $C_{1-6}$ alkyl (including cycloalkyl and cycloalkylalkyl), $C_{1-4}$ alkoxy, pyrryl, thienyl, pyridyl, 1,3-benzodioxolo, phenyl and naphthyl, which groups are optionally substituted by one or more atoms or groups independently selected from halogen, cyano, nitro, carboxyl, phenyl, phenoxy, benzyloxy, $-COR^{11}$, $-CO_2R^{11}$, $-CONR^{11}R^{12}$, $-CH_2OR^{11}$, $-NR^{11}R^{12}$, $-NHCOR^{11}$, $-NHSO_2R^{11}$, $-SR^{11}$, $-SO_2R^{11}$, $-SO_3R^{11}$ (wherein $R^{11}$ and $R^{12}$ are as hereinbefore defined) $-O(CH_2)_pNR^{11}R^{12}$, $-O(CH_2)_pN^+R^{11}R^{12}R^{13}$ and $-O(CH_2)_pSO_3R^{11}$ (wherein p, $R^{11}$ and $R^{12}$ are as hereinbefore defined and $R^{13}$ is hydrogen or $C_{1-6}$ alkyl);

$R^3$ is hydrogen, OH, $C_{1-6}$ alkyl, $C_{1-6}$ alkoxy or $-O C_{1-6}$ acyl:

$R^4$ is a group independently selected from $C_{1-6}$ alkyl (including cycloalkyl and cycloalkylalkyl), $C_{2-6}$ alkenyl, and $C_{2-6}$ alkynyl which groups are optionally substituted by one or more atoms or groups independently selected from halogen, oxo, $C_{1-4}$ alkoxy, $-CO_2R^{14}$, $-NR^{14}R^{15}$, $-SR^{14}$, $-S(O)C_{1-6}$ alkyl, $-SO_2R^{14}$, and $-SO_3R^{14}$ (wherein $R^{14}$ and $R^{15}$ are as hereinbefore defined);

$R^5$ is a group independently selected from $C_{2-6}$ alkyl (including cycloalkyl and cycloalkylalkyl), $C_{2-6}$ alkenyl and $C_{2-6}$ alkynyl, which groups are optionally substituted by one or more atoms or groups independently selected from halogen, oxo $C_{1-4}$ alkoxy, $-CO_2R^{14}$, $-NR^{14}R^{15}$, $-SR^{14}$, $-S(O)C_{1-6}$ alkyl, $-SO_2R^{14}$, $-SO_3R^{14}$ (wherein $R^{14}$ and $R^{15}$ are as hereinbefore defined);

or $R^4$ and $R^5$, together with the carbon atom to which they are attached, form a $C_{3-7}$ spiro cycloalkyl group which is optionally substituted by one or more atoms or groups independently selected from halogen, $C_{1-6}$ alkoxy, $-CO_2R^{14}$, $-SO_3R^{14}$ and $-NR^{14}R^{15}$ (where $R^{14}$ and $R^{15}$ are as hereinbefore defined);

$R^6$ and $R^7$ are independently selected from hydrogen and $C_{1-6}$ alkyl; and X is an aromatic or non-aromatic monocyclic or bicyclic ring system having from 5 to 10 carbon atoms (including the two carbon atoms forming part of the thiazepine ring) wherein optionally one or more of the carbon atoms is/are replaced by heteroatom(s) independently selected from nitrogen, oxygen and sulphur;

or X is an aromatic or non-aromatic monocyclic or bicyclic ring system having from 5 to 10 carbon atoms (including the two carbon atoms forming part of the thiazepine ring) wherein one or more of the carbon atoms is/are replaced by heteroatom(s) independently selected from nitrogen, oxygen and sulphur.

With the proviso that when l is an integer of from 0 to 4, $R^1=R^6=R^7=H$, $R^3=H$ or OH, $R^2=$ unsubstituted phenyl or phenyl substituted by one or more atoms or groups independently selected from halogen, nitro, phenylalkoxy, $C_{1-4}$ alkoxy, $C_{1-6}$ alkyl and —O(CH$_2$)$_p$SO$_3$R$^{11}$ wherein p and R$^{11}$ are as hereinbefore defined, wherein said phenylalkoxy, alkoxy and alkyl groups are optionally substituted by one or more halogen atoms, and X is a fused phenyl ring, then R$^4$ is other than a $C_{1-6}$ straight alkyl group and R$^5$ is other than a $C_{2-5}$ straight alkyl group; and salts, solvates and physiologically functional derivatives thereof.

Preferably the present invention provides a compound of formula (Ia):

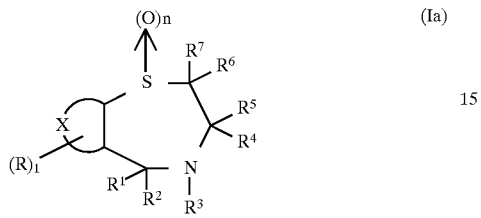

wherein l is an integer of from 0 to 4;

n is an integer of from 0 to 2;

R is an atom or group selected from halogen, cyano, nitro, alkyl, alkoxy, aryl, heteroaryl, aryloxy, arylalkoxy, aralkyl, alkaryl, —COR$^{11}$, —CO$_2$R$^{11}$, —CONR$^{11}$R$^{12}$, —CH$_2$OR$^{11}$, —NR$^{11}$R$^{12}$, —NHCOR$^{11}$, —NHSO$_2$R$^{11}$, —SR$^{11}$, —SO$_2$R$^{11}$, —SO$_3$R$^{11}$ wherein R$^{11}$ and R$^{12}$ are independently selected from hydrogen, $C_{1-6}$ alkyl and phenyl, wherein said alkyl, alkoxy, aryl, heteroaryl, aryloxy, arylalkoxy, aralyl and alkaryl groups are optionally substituted by one or more atoms or groups selected from halogen, nitro, nitrile, alkyl, alkoxy, —COR$^{11}$, —CO$_2$R$^{11}$, —SO$_3$R$^{11}$ wherein R$^{11}$ is as hereinbefore defined and —NR$^{14}$R$^{15}$ wherein R$^{14}$ and R$^{15}$ are as hereinbefore defined;

R$^1$ and R$^3$ are independently selected from hydrogen and $C_{1-6}$ alkyl;

R$^2$ is an atom or group selected from hydrogen, $C_{1-6}$ alkyl (including cycloalkyl and cycloalkylalkyl), $C_{1-4}$ alkoxy, pyrryl, thienyl, pyridyl, 1,3-benzodioxolo, phenyl and naphthyl, which groups are optionally substituted by one or more atoms or groups independently selected from halogen, cyano, nitro, carboxyl, phenyl, phenoxy, benzyloxy, —COR$^{11}$, —CO$_2$R$^{11}$, —CONR$^{11}$R$^{12}$, —CH$_2$OR$^{11}$, —NR$^{11}$R$^{12}$, —NHCOR$^{11}$, —NHSO$_2$R$^{11}$, —SR$^{11}$, —SO$_2$R$^{11}$, —SO$_3$R$^{11}$ (wherein R$^{11}$ and R$^{12}$ are independently selected from hydrogen, $C_{1-6}$ alkyl and phenyl), —O(CH$_2$)$_p$NR$^{11}$R$^{12}$, —O(CH$_2$)$_p$N$^+$R$^{11}$R$^{12}$R$^{13}$ and —O(CH$_2$)$_p$SO$_3$R$^{11}$ (wherein p is an integer of from 1 to 4, R$^{11}$ and R$^{12}$ are as hereinbefore defined and R$^{13}$ is hydrogen or $C_{1-6}$ alkyl);

R$^4$ is a group independently selected from $C_{1-6}$ alkyl (including cycloalkyl and cycloalkylalkyl), $C_{2-6}$ alkenyl and $C_{2-6}$ alkynyl, which groups are optionally substituted by one or more atoms or groups independently selected from halogen, $C_{1-4}$ alkoxy, —CO$_2$R$^{14}$, —NR$^{14}$R$^{15}$, —SO$_3$R$^{14}$ (wherein R$^{14}$ and R$^{15}$ are independently selected from hydrogen and $C_{1-6}$ alkyl) and R$^{16}$COR$^{17}$ where R$^{16}$ is a $C_{1-4}$ alkylene group and R$^{17}$ is a $C_{1-4}$ alkyl group;

R$^5$ is a group independently selected from $C_{2-6}$ alkyl (including cycloalkyl and cycloalkylalkyl), $C_{2-6}$ alkenyl and $C_{2-6}$ alkynyl, which groups are optionally substituted by one or more atoms or groups indepen- dently selected from halogen, $C_{1-4}$ alkoxy, —CO$_2$R$^{14}$, —NR$^{14}$R$^{15}$, —SO$_3$R$^{14}$ (wherein R$^{14}$ and R$^{15}$ are independently selected from hydrogen and $C_{1-6}$ alkyl) and —R$^{16}$COR$^{17}$ where R$^{16}$ is a $C_{1-4}$ alkylene group and R$^{17}$ is a $C_{1-4}$ alkyl group;

or R$^4$ and R$^5$, together with the carbon atom to which they are attached, form a $C_{3-7}$ spiro cycloalkyl group which is optionally substituted by one or more atoms or groups independently selected from halogen, $C_{1-6}$ alkoxy, —CO$_2$R$^{14}$, —SO$_3$R$^{14}$ and —NR$^{14}$R$^{15}$ (where R$^{14}$ and R$^{15}$ are as hereinbefore defined;

R$^6$ and R$^7$ are independently selected from hydrogen and $C^{1-6}$ alkyl; and X is an aromatic or non-aromatic monocyclic or bicyclic ring system having from 5 to 10 carbon atoms (including the two carbon atoms forming part of the thiazepine ring) wherein optionally one or more of the carbon atoms is/are replaced by heteroatom(s) independently selected from nitrogen, oxygen and sulphur;

with the proviso that when l is an integer of from 0 to 4, R$^1$=R$^3$=R$^6$=R$^7$=H, R$^2$= unsubstituted phenyl or phenyl substituted by one or more atoms or groups independently selected from halogen, nitro, phenylalkoxy, $C_{1-4}$ alkoxy, $C_{1-6}$ alkyl and —O(CH$_2$)$_p$ SO$_3$R$^{11}$ wherein p and R$^{11}$ are as hereinbefore defined, wherein said phenylalkoxy, alkoxy and alkyl groups are optionally substituted by one or more halogen atoms, and X is a fused phenyl ring, then R$^4$ is other than a $C_{1-6}$ straight alkyl group and R$^5$ is other than a $C_{2-5}$ straight alkyl group; and salts, solvates and physiologically functional derivatives thereof.

Pharmaceutically acceptable salts are particularly suitable for medical applications because of their greater aqueous solubility relative to the parent, ie basic, compounds. Such salts must clearly have a pharmaceutically acceptable anion or cation. Suitable pharmaceutically acceptable acid addition salts of the compounds of the present invention include those derived from inorganic acids, such as hydrocholoric, hydrobromic, phosphoric, metaphosphoric, nitric, sulphamic and sulphuric acids, and organic acids such as acetic, benzenesulphonic, benzoic, citric, ethanesulphonic, fumaric, gluconic, glycollic, isothionic, lactic, lactobionic, maleic, malic, methanesulphonic, succinic, p-toluenesulphonic, tartaric and trifluoroacetic acids. The chloride salt is particularly preferred for medical purposes. Suitable pharmaceutically acceptable base salts include ammonium salts, alkali metal salts, such as sodium and potassium salts, and alkaline earth salts, such as magnesium and calcium salts.

Salts having a non-pharmaceutically acceptable anion are within the scope of the invention as useful intermediates for the preparation or purification of pharmaceutically acceptable salts and/or for use in non-therapeutic, for example, in vitro, applications.

The term "physiologically functional derivative" as used herein refers to any physiologically acceptable derivative of a compound of the present invention, for example, an ester, which upon administration to mammal, such as a human, is capable of providing (directly or indirectly) such a compound or an active metabolite thereof.

A further aspect of the present invention is prodrugs of the compounds of the invention. Such prodrugs can be metabolised in vivo to give a compound according to the invention. These prodrugs may or may not be active in their own right.

The compounds of the present invention can also exist in different polymorphic forms, for example amorphous and crystalline polymorphic forms. All polymorphic forms of the compounds of the present invention are within the scope of the invention and are a further aspect thereof.

The term "alkyl" as used herein refers, unless otherwise stated, to a monovalent straight or branched chain radical. Likewise, the term "alkoxy" refers to a monovalent straight or branched chain radical attached to the parent molecular moiety through an oxygen atom. The term "aryl" refers to an aromatic monocyclic or bicyclic ring system comprising from 6 to 10 carbon atoms and optionally substituted by one or more atoms or groups selected from halogen, nitro, nitrile, alkyl, alkoxy, —$COR^{11}$, —$CO_2R^{11}$, —$SO_3R^{11}$ wherein $R^{11}$ is as hereinbefore defined and —$NR^{14}R^{15}$ wherein $R^{14}$ and $R^{15}$ are as hereinbefore defined. The term "heteroaryl" refers to an aromatic monocyclic or bicyclic ring system comprising from 5 to 10 carbon atoms wherein one or more of the carbon atoms is/are replaced by heteroatom(s) independently selected from nitrogen, oxygen and sulphur which ring system is optionally substituted by one or more atoms or groups selected from halogen, nitro, nitrile, alkyl, alkoxy, —$COR^{11}$, —$CO_2R^{11}$, —$SO_3R^{11}$ wherein $R^{11}$ is as hereinbefore defined and —$NR^{14}R^{15}$ wherein $R^{14}$ and $R^{15}$ are as hereinbefore defined. The term "aryloxy" refers to an aryl group as herein defined attached to the parent molecular moiety through an oxygen atom. The term "arylalkoxy" refers to an aryl group as herein defined attached to a divalent $C_{1-6}$ alkylene group which is itself attached to the parent molecular moiety through an oxygen atom. The term "aralkyl" refers to an aryl group as herein defined attached to a divalent $C_{1-6}$ alkylene group which is itself attached to the parent molecular moiety. The term "alkaryl" refers to an alkyl group as herein defined attached to an aryl group as herein defined which is itself attached to the parent molecular moiety. The term "halogen" refers to Fluorine, Chlorine, Bromine and Iodine.

The compounds of formula (I) can exist in forms wherein one or more of the carbon centres —$C(R^6)(R^7)$—, —$C(R^4)(R^5)$— and —$C(R^1)(R^2)$— is/are chiral. The present invention includes within its scope each possible optical isomer substantially free, ie associated with less than 5%, of any other optical isomer(s), and mixtures of one or more optical isomers in any proportions, including racemic mixtures.

For the purposes of this specification, the absolute chiralities of —$C(R^4)(R^5)$— and —$C(R^1)(R^2)$— are given in the order —$C(R^4)(R^5)$—, then —$C(R^1)(R^2)$—. For example, the prefix "(RS)—" denotes an (R)-configuration at —$C(R^4)(R^5)$— and an (S)-configuration at —$C(R^1)(R^2)$— and the prefix "(RS,SR)—" denotes a mixture of two isomers wherein one is (R)— at —$C(R^4)(R^5)$— and (S)— at —$C(R^1)(R^2)$ and the other is (S)— at —$C(R^4)(R^5)$— and (R)— at —$C(R^1)(R^2)$. Other permutations will be clear to the skilled person.

In those cases where the absolute stereochemistry at —$C(R^4)(R^5)$— and —$C(R^1)(R^2)$— has not been determined, the compounds of the invention are defined in terms of the relative positions of the $R^4/R^5$ and $R^1/R^2$ substituents. Thus those compounds wherein the bulkier of the $R^4$ and $R^5$ substituents, ie the substituent of higher mass, and the bulkier of the $R^1$ and $R^2$ substituents are both located on the same side of the thiazepine ring are referred to herein as "cis", and those compounds wherein the two bulkier substituents are located on opposite sides of the ring are referred to as "trans". It will be evident to a skilled person that both "cis" and "trans" compounds of the invention can each exist in two enantiomeric forms which are individually designated "(+)-" or "(−)-" according to the direction of rotation of a plane of polarised light when passed through a sample of the compound. Cis or trans compounds of the invention in which the individual enantiomers have not been resolved are referred to herein using the prefix "(±)-".

Preferred compounds of formula (I) having particularly desirable hypolipidaemic properties are the trans isomers of those compounds wherein l is 0.1, or 2;

n is 1 or 2;

$R^1$, $R^6$ and $R^7$ are all hydrogen; and $R^3$ is hydrogen or hydroxy; and

X is a fused phenyl, naphthyl, pyrryl, thienyl, or pyridyl group;

Of these compounds, those wherein l is 0 or 1;

n is 2; and $R^2$ is a group selected from pyrryl, thienyl, pyridyl, phenyl and naphthyl, which groups may be substituted by one or more atoms or groups independently selected from halogen, cyano, nitro, carboxyl, phenyl, phenoxy, benzyloxy, —$COR^{11}$, —$CO_2R^{11}$, —$CONR^{11}R^{12}$, —$CH_2OR^{11}$, —$NR^{11}R^{12}$, —$NHCOR^{11}$, —$NHSO_2R^{11}$, —$SR^{11}$, —$SO_2R^{11}$, —$SO_3R^{11}$ (wherein $R^{11}$ and $R^{12}$ are independently selected from hydrogen, $C_{1-6}$ alkyl and phenyl), —$O(CH_2)_pNR^{11}R^{12}$, —$O(CH_2)_pN^+R^{11}R^{12}R^{13}$ and —$O(CH_2)_pSO_3R^{11}$ (wherein p is an integer of from 1 to 4, $R^{11}$ and $R^{12}$ are as hereinbefore defined and $R^{13}$ is hydrogen or $C_{1-6}$ alkyl);

are particularly preferred.

Compounds of formula (I) having exceptional hypolipidaemic properties include:

(−)-(RR)-3-butyl-3-ethyl-2,3,4,5-tetrahydro-5-phenyl-1,4-benzothiazepine 1,1-dioxide;

(±)-trans-3-((E)-2-butenyl)-3-ethyl-2,3,4,5-tetrahydro-5-phenyl-1,4-benzothiazepine 1,1-dioxide;

(±)-trans-3-ethyl-2,3,4,5-tetrahydro-3-(3-methoxypropyl)-5-phenyl-1,4-benzothiazepine 1,1-dioxide;

(±)-trans-1-(3-ethyl-2,3,4,5-tetrahydro-5-phenyl-1,4-benzothiazepin-3-yl)-2-butanone S,S-dioxide;

(±)-trans-1-(3-ethyl-2,3,4,5-tetrahydro-8-methoxy-5-phenyl-1,4-benzothiazepin-3-yl)-2-butanone S,S-dioxide hydrochloride 1,1 hydrate;

(±)-trans-3-(1-butenyl)-3-ethyl-2,3,4,5-tetrahydro-5-phenyl-1,4-benzothiazepine 1,1-dioxide hydrochloride 0.4 hydrate;

(±)-trans-3-(ethoxyethyl)-3-ethyl-2,3,4,5-tetrahydro-5-phenyl-1,4-benzothiazepine 1,1-dioxide hydrochloride hemihydrate;

(±)-trans-3-(ethoxymethyl)-3-ethyl-2,3,4,5-tetrahydro-5-phenyl-1,4-benzothiazepine 1,1-dioxide hydrochloride;

(±)-trans-ethyl 3-(3-ethyl-2,3,4,5-tetrahydro-5-phenyl-1,4-benzothiazepin-3-yl)propionate 1,1-dioxide;

(±)-trans-(E)-4-(3-ethyl-2,3,4,5-tetrahydro-5-phenyl-1,4-benzothiazepin-3-yl)-3-buten-2-one 1,1-dioxide;

(±)-2,3,4,5-tetrahydro-8-methoxy-5-phenylspiro(1,4-benzothiazepine-3,1-cyclohexane) 1,1-dioxide;

(±)-trans-3-butyl-3-ethyl-2,3,4,5-tetrahydro-5-(4-pyridyl)-1,4-benzothiazepine 1,1-dioxide;

(±)-trans-3-butyl-3-ethyl-2,3,4,5-tetrahydro-4-hydroxy-5-(4-pyridyl)-1,4-benzothiazepine 1,1-dioxide;

(±)-trans-3-butyl-3-ethyl-2,3,4,5-tetrahydro-5-(2-thienyl)-1,4-benzothiazepine 1,1-dioxide;

(±)-trans-3-butyl-3-ethyl-2,3,4,5-tetrahydro-5-(1H-pyrrol-1-yl)-1,4-benzothiazepine 1,1-dioxide;

(±)-trans-3-butyl-3-ethyl-2,3,4,5-tetrahydro-5-phenylpyrido (4,3-F)-1,4-benzothiazepine 1,1-dioxide;

(±)-trans-3-butyl-3-ethyl-3,4,5,7-tetrahydro-5-phenyl-2H-pyrrolo(3,4-F)-1,4-benzothiazepine 1,1-dioxide 0.1 hydrate;
(±)-trans-3-butyl-3-ethyl-2,3,4,5-tetrahydro-5-phenylthieno(2,3-F)-1,4-benzothiazepine 1,1-dioxide;
(±)-trans-3-ethyl-2,3,4,5-tetrahydro-5-phenyl-3-(4,4,4-trifluorobutyl)-1,4-benzothiazepine 1,1-dioxide;
(±)-trans-2,3,4,5-tetrahydro-3-isopropyl-3-methyl-5-phenyl-1,4-benzothiazepine 1,1-dioxide 0.25 H$_2$O;
(±)-trans-3-((E)-2-Butenyl)-3-ethyl-2,3,4,5-tetrahydro-5-phenyl-1,4-benzothiazepine;
(±)-Cis-2,3,4,5-Tetrahydro-3-isopropyl-3-methyl-5-phenyl-1,4-benzothiazepine 1,1-dioxide 0.66 H$_2$O;
(±)-trans-3-(3-Ethyl-2,3,4,5-tetrahydro-5-phenyl-1,4-benzothiazepin-3-yl)propanol 1,1 dioxide;
(±)-trans-3-Ethyl-5-(4-Fluorophenyl)-2,3,4,5-tetrahydro-7-methoxy-3-(3-methoxypropyl)-1,4-benzothiazepine 1,1-dioxide hydrochloride;
(±)-2,3,4,5-Tetrahydro-7-methoxy-5-phenylspiro(1,4-benzothiazepine-3,1-cyclohexane) 1,1-dioxide;
(±)-trans-1-(3-Ethyl-2,3,4,5-tetrahydro-7-methoxy-5-phenyl-1,4-benzothiazepin-3-yl)-2-butanone S,S-dioxide hydrochloride;
(±)trans-3-butyl-3-ethyl-2,3,4,5-tetrahydro-5-phenylnaphtho(3,2-F)-1,4-benzothiazepine 1,1-dioxide;
(±)-trans-1-(3-Ethyl-2,3,4,5-tetrahydro-7,8-dimethoxy-5-phenyl-1,4-benzothiazepin-3-yl)-2-butanone S,S-dioxide;
(±)-trans-3-(1-butenyl)-3-ethyl-2,3,4,5-tetrahydro-7,8-dimethoxy-5-phenyl-1,4-benzothiazepine 1,1-dioxide;
(±)-trans-1-(3-Ethyl-2,3,4,5-tetrahydro-7,8-dimethoxy-5-phenyl-1,4-benzothiazepin-3-yl)-3-butanone S,S-dioxide;
(±)-trans-1-(3-Ethyl-2,3,4,5-tetrahydro-8-methoxy-5-phenyl-1,4-benzothiazepin-3-yl)-1-butanone S,S-dioxide;
(±)-trans-1-(3-Ethyl-2,3,4,5-tetrahydro-7,8-dimethoxy-5-phenyl-1,4-benzothiazepin-3-yl)-1-butanone S,S-dioxide;
(±)-trans-1-(3-ethyl-2,3,4,5-tetrahydro-7,8-dimethoxy-5-phenyl-1,4-benzothiazepin-3-yl)-4,4,4-trifluoro-1-butanone S,S-dioxide;
(±)-trans-1-(3-ethyl-2,3,4,5-tetrahydro-7,8-dimethoxy-5-phenyl-1,4-benzothiazepin-3-yl)-3,3,4,4,4-pentafluoro-2-butanone S,S-dioxide;
(±)-trans-1-(3-ethyl-2,3,4,5-tetrahydro-7,8-dimethoxy-5-phenyl-1,4-benzothiazepin-3-yl)-4,4,4-trifluoro-2-butanone S,S-dioxide;
(±)-trans-3-ethyl-2,3,4,5-tetrahydro-7,8-dimethoxy-5-phenyl-3-(4,4,4-trifluorobutyl)-1,4-benzothiazepine 1,1-dioxide;
(±)-trans-1-(3-(2,2,2-trifluoroethyl)-2,3,4,5-tetrahydro-7,8-dimethoxy-5-phenyl-1,4-benzothiazepin-3-yl)-2-butanone S,S-dioxide:
(±)-trans-1-(3-Ethyl-2,3,4,5-tetrahydro-7,8-diethoxy-5-phenyl-1,4-benzothiazepin-3-yl)-2-butanone S,S-dioxide;
(±)-trans-3-((3-ethyl-2,3,4,5-tetrahydro-3-(2-oxobutyl)-5-phenyl-1,4-benzothiazepin-8-yl)oxy)propanesulfonic acid 1,1-dioxide;
(±)-trans-2-((3-ethyl-2,3,4,5-tetrahydro-3-(2-oxobutyl)-5-phenyl-1,4-benzothiazepin-8-yl)oxy)ethyltrimethylammonium iodide 1,1-dioxide;
Of these the following compounds are most preferred:
(−)-(RR)-3-butyl-3-ethyl-2,3,4,5-tetrahydro-5-phenyl-1,4-benzothiazepine 1,1-dioxide;
(±)-trans-1-(3-ethyl-2,3,4,5-tetrahydro-8-methoxy-5-phenyl-1,4-benzothiazepin-3-yl)-2-butanone S,S-dioxide hydrochloride 1,1 hydrate;
(±)-Cis-2,3,4,5-Tetrahydro-3-isopropyl-3-methyl-5-phenyl-1,4-benzothiazepine 1,1-dioxide 0.66 H$_2$O;
(±)-trans-1-(3-Ethyl-2,3,4,5-tetrahydro-7,8-dimethoxy-5-phenyl-1,4-benzothiazepin-3-yl)-2-butanone S,S-dioxide;

According to further aspects of the invention, there are also provided:
(a) compounds of formula (I) and pharmaceutically acceptable salts, solvates and physiologically functional derivatives thereof for use as therapeutic agents, particularly in the prophylaxis and treatment of clinical conditions for which a bile acid uptake inhibitor is indicated, for example, a hyperlipidaemic condition such as atherosclerosis;
(b) Pharmaceutical compositions comprising a compound of formula (I) or one of its pharmaceutically acceptable salts, solvates, or physiologically functional derivatives, at least one pharmaceutically acceptable carrier and, optionally, one or more other physiologically active agents;
(c) the use of a compound of formula (I) or of a pharmaceutically acceptable salt, solvate, or physiologically functional derivative thereof in the manufacture of a medicament for the prophylaxis or treatment of a clinical condition for which a bile acid uptake inhibitor is indicated, for example, a hyperlipidaemic condition, such a atherosclerosis;
(d) a method of inhibiting the absorption of bile acids from the intestine of a mammal, such as a human, which comprises administering an effective bile acid absorption inhibiting amount of a compound of formula (I) or of a pharmaceutically acceptable salt, solvate, or physiologically functional derivative thereof to the mammal;
(e) a method of reducing the blood plasma or serum concentrations of LDL and VLDL cholesterol in a mammal, such as a human, which comprises administering an effective cholesterol reducing amount of a compound of formula (I) or of a pharmaceutically acceptable salt, solvate, or physiologically functional derivative thereof to the mammal;
(f) a method of reducing the concentrations of cholesterol and cholesterol ester in the blood plasma or serum of a mammal, such as a human, which comprises administering an effective cholesterol and cholesterol ester reducing amount of a compound of formula (I) or of a pharmaceutically acceptable salt, solvate, or physiologically functional derivative thereof to the mammal;
(g) a method of increasing the faecal excretion of bile acids in a mammal, such as a human, which comprises administering an effective bile acid faecal extraction increasing amount of a compound of formula (I) or of a pharmaceutically acceptable salt, solvate, or physiologically functional derivative thereof to the mammal;
(h) a method for the prophylaxis or treatment of a clinical condition in a mammal, such as a human, for which a bile acid uptake inhibitor is indicated, for example, a hyperlipidaemic condition, such as atherosclerosis, which comprises administering a therapeutically effective amount of a compound of the formula (I) or of a pharmaceutically acceptable salt, solvate, or physiologically functional derivative thereof to the mammal;
(i) a method of reducing the incidence of coronary heart disease-related events in a mammal, such as a human, which comprises adminstering an effective coronary heart disease-related events reducing amount of a compound of formula (I) or of a pharmaceutically acceptable salt, solvate, or physiologically functional derivative thereof;
(j) a method of reducing the concentration of cholesterol in the blood plasma or serum of a mammal, such as a human, which comprises administering an effective cholesterol reducing amount of a compound of formula (I);

(k) processes for the preparation of compounds of formula (I) (including salts, solvates and physiologically functional derivatives thereof as defined herein); and (l) Compounds of formula (II) for use as intermediates in the preparation of compounds of formula (I).

Hereinafter all references to "compound(s) of formula (I)" refer to compound(s) of formula (I) as described above together with their salts, solvates and physiologically functional derivatives as defined herein.

The amount of a compound of formula (I) which is required to achieve the desired biological effect will, of course, depend on a number of factors, for example, the specific compound chosen, the use for which it is intended, the mode of administration and the clinical condition of the recipient. In general, a daily dose is in the range of from 0.0001 mg to 100 mg, typically from 0.0001 mg to 5 mg, per day per kilogram bodyweight, for example, 0.005–0.5 mg/kg/day, preferably 0.001 mg to 0.5 mg/kg/day. An intravenous dose can, for example, be in the range of from 0.001 mg to 0.5 mg/kg, which can conveniently be administered as an infusion of from 0.03 ng to 50 ng per kilogram per minute. Infusion fluids suitable for this purpose can contain, for example, from 0.0003 ng to 5 mg, typically from 0.003 ng to 5 mg, per milliliter. Unit doses can contain, for example, from 0.01 mg to 10 mg of the active compound, preferably from 0.1 to 5 mg. Thus ampoules for injection can contain, for example, from 0.01 mg to 100 mg and orally administrable unit dose formulations, such as tablets or capsules, can contain, for example, from 0.01 to 1000 mg, typically from 0.01 to 60 mg, preferably from 0.1 mg to 10 mg. In the case of pharmaceutically acceptable salts, the weights indicated above refer to the weight of the benzothiazepine ion derived from the salt.

For the prophylaxis or treatment of the conditions referred to above, the compounds of formula (I) can be used as the compound per se, but are preferably presented with an acceptable carrier in the form of a pharmaceutical composition. The carrier must, of course, be acceptable in the sense of being compatible with the other ingredients of the composition and must not be deleterious to the recipient. The carrier can be a solid or a liquid, or both, and is preferably formulated with the compound as a unit-dose composition, for example, a tablet, which can contain from 0.05% to 95% by weight of the active compound. Other pharmacologically active substances can also be present including other compounds of formula (I). The pharmaceutical compositions of the invention can be prepared by any of the well known techniques of pharmacy consisting essentially of admixing the components.

Pharmaceutical compositions according to the present invention include those suitable for oral, rectal, topical, buccal (e.g. sub-lingual) and parenteral (e.g. subcutaneous, intramuscular, intradernal, or intravenous) administration, although the most suitable route in any given case will depend on the nature and severity of the condition being treated and on the nature of the particular compound of formula (I) which is being used. Enteric-coated and enteric-coated controlled release formulations are also within the scope of the invention. Suitable enteric coatings include cellulose acetate phthalate, polyvinylacetate phthalate, hydroxypropylmethylcellulose phthalate and anionic polymers of methacrylic acid and methacrylic acid methyl ester.

Pharmaceutical compositions suitable for oral administration can be presented in discrete units, such as capsules, cachets, lozenges, or tablets, each containing a predetermined amount of a compound of formula (I); as a powder or granules; as a solution or a suspension in an aqueous or non-aqueous liquid; or as an oil-in-water or water-in-oil emulsion. As indicated, such compositions can be prepared by any suitable method of pharmacy which includes the step of bringing into association the active compound and the carrier (which can constitute one or more accessory ingredients). In general, the compositions are prepared by uniformly and intimately admixing the active compound with a liquid or finely divided solid carrier, or both, and then, if necessary, shaping the product. For example, a tablet can be prepared by compressing or moulding a powder or granules of the compound, optionally with one or more assessory ingredients. Compressed tablets can be prepared by compressing, in a suitable machine, the compound in a free-flowing form, such as a powder or granules optionally mixed with a binder, lubricant, inert diluent and/or surface active/dispersing agent(s). Moulded tablets can be made by moulding, in a suitable machine, the powdered compound moistened with an inert liquid diluent.

Pharmaceutical compositions suitable for buccal (sublingual) administration include lozenges comprising a compound of formula (I) in a flavoured base, usually sucrose and acacia or tragacanth, and pastilles comprising the compound in an inert base such as gelatin and glycerin or sucrose and acacia.

Pharmaceutical compositions suitable for parenteral administration conveniently comprise sterile aqueous preparations of a compound of formula (I), preferably isotonic with the blood of the intended recipient. These preparations are preferably administered intravenously, although administration can also be effected by means of subcutaneous. intramuscular, or intradermal injection. Such preparations can conveniently be prepared by admixing the compound with water and rendering the resulting solution sterile and isotonic with the blood. Injectable compositions according to the invention will generally contain from 0.1 to 5% w/w of the active compound.

Pharmaceutical compositions suitable for rectal administration are preferably presented as unit-dose suppositories. These can be prepared by admixing a compound of formula (I) with one or more conventional solid carriers, for example, cocoa butter, and then shaping the resulting mixture.

Pharmaceutical compositions suitable for topical application to the skin preferably take the form of an ointment, cream, lotion, paste, gel, spray, aerosol, or oil. Carriers which can be used include vaseline, lanoline, polyethylene glycols, alcohols, and combinations of two or more thereof. The active compound is generally present at a concentration of from 0.1 to 15% w/w of the composition, for example, from 0.5 to 2%.

Transdermal adminstration is also possible. Pharmaceutical compositions suitable for transdermal administration can be presented as discrete patches adapted to remain in intimate contact with the epidermis of the recipient for a prolonged period of time. Such patches typically contain the active compound in an optionally buffered, aqueous solution, dissolved and/or dispersed in an adhesive, or dispersed in a polymer. A suitable concentration of the active compound is about 1% to 35%, preferably about 3% to 15%. As one particular possibility, the active compound can be delivered from the patch by electrotransport or iontophoresis, for example, as described in *Pharmaceutical Research,* 3(6), 318 (1986).

The compounds of the invention can be prepared by conventional methods known to a skilled person or in an analogous manner to processes described in the art.

For example, compounds of formula (I) wherein n=0 and $R^1$ and $R^3$ are hydrogen can be prepared by reducing the imine bond of a compound of formula (II)

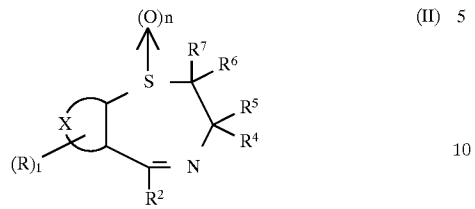

wherein l, R, $R^2$, $R^4$ to $R^7$ and X are as hereinbefore defined, using, for example, a metal hydride compound, such as borane, in a suitable solvent, such as THF, or when n is 1 or 2 in formula (I) catalytic hydrogenation using, for example, a palladium catlalyst, such as 10% Pd/C.

Compounds of formula (II) as herein defined are considered to be novel and constitute a further aspect of the present invention.

Compounds of formula (II) can be prepared by cyclising compounds of formula (III)

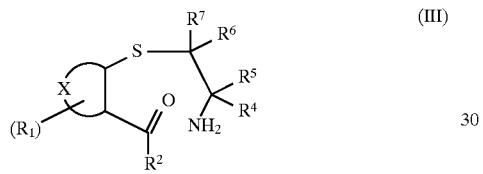

Wherein l, R, $R^2$, $R^4$ to $R^7$ and X are as hereinbefore defined, by, for example, azeotropic distillation or refluxing in the presence of a suitable drying agent, such as molecular sieves, in a suitable solvent, for example, 2,6-lutidine, in the presence of an acid, such as HCl.

Compounds of formula (III) can be prepared by reacting a compound of formula (IV)

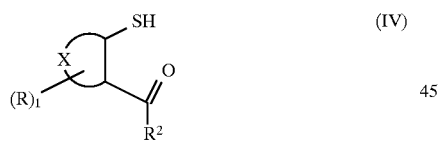

wherein l, R, $R^2$ and X are as hereinbefore defined, with a compound of formula (V) or preferably with a compound of formula (Va)

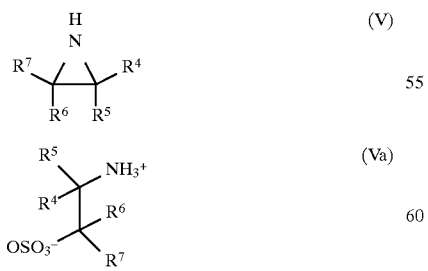

wherein $R^4$ to $R^7$ are as hereinbefore defined, typically in a polar solvent, for example, methanol.

Compounds of formula (IV) can be prepared by hydrolysis of a compound of formula (XXII):

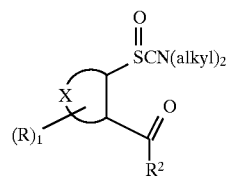

wherein l, X, R and $R^2$ are as hereinbefore defined with, for example, a base such as KOH in methanol/THF. Preferably alkyl is methyl or ethyl.

Compounds of formula (XXII) can be prepared by heating of a compound of formula (XXIII)

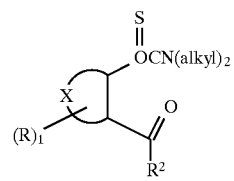

wherein l, X, R and $R^2$ are as hereinbefore defined in a non-polar solvent such as $(Ph)_2O$.

Compounds of formula (XXIII) can be prepared by reaction of a compound of formula (XXIV)

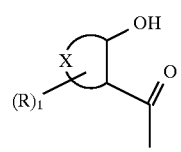

wherein l, X, R and $R^2$ are as hereinbefore defined, with halo-$CSN(alkyl)_2$, for example, Cl CS $NMe_2$ in a suitable solvent such as $DMAP/Et_3N$.

Compounds of formula (III) can also be prepared by reacting a compound of formula (XVIII)

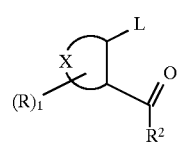

Wherein l, R, $R^2$ and X are as hereinbefore defined and L is a suitable leaving group, for example, halogen, with a compound of formula $HSC(R^6)(R^7)C(R^4)(R^5)NH_2$ wherein $R^4$ to $R^7$ are as hereinbefore defined.

Compounds of formula (XVIII) can be prepared by reacting a compound of formula (XIX)

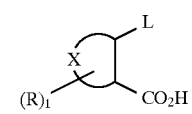

wherein l, L, R and X are as hereinbefore defined, with a compound of formula $R^2H$ wherein $R^2$ is as hereinbefore defined, typically by a Friedel-Crafts reaction using, for example, aluminium chloride.

Alternatively, compounds of formula (XVII) can be prepared by reacting a compound of formula (XVIIIa)

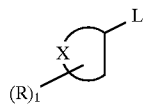 (XVIIIa)

wherein l, L, R and X are as hereinbefore defined with a suitable acid halide, e.g. $R^2COCl$ wherein $R^2$ is as hereinbefore defined, by a Friedel-Gafts reaction using, for example, aluminum chloride.

Compounds of formula (III) wherein $R^4$ is —$CH_2OH$ can also be prepared by hydrolysis, preferably with base, of a compound of formula (XVIIa)

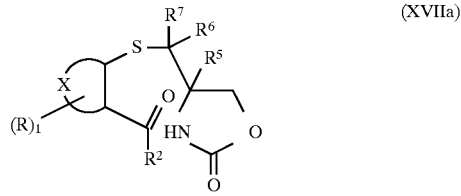 (XVIIa)

wherein l, R, $R^2$ $R^5$ to $R^7$ and X are as hereinbefore defined, using, for example, KOH in aqe. ethanol.

Compounds of formula (XVII) can be prepared by reacting a compound of formula (IV) wherein m, R, $R^2$ and X are as hereinbefore defined, with a compound of formula (XII)

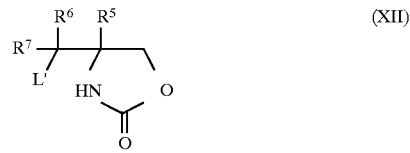 (XII)

wherein $R^5$ to $R^7$ are as hereinbefore defined and L' is a suitable leaving group, for example, —OTosyl, typically in a polar aprotic solvent, such as DMF, in the presence of a base, for example, NaH.

Compounds of formula (IV) can be prepared by reacting a compound of formula (VI)

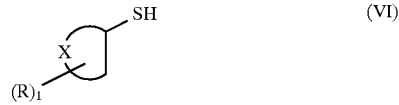 (VI)

wherein l, R and X are as hereinbefore defined, with a compound of formula $R^2CN$ wherein $R^2$ is as hereinbefore defined. The reaction is typically carried out by metalation of compound (VI) using, for example, n-butyl lithium in the presence of N,N,N',N'-tetramethylethylenediamine (TMEDA) followed by reaction with the appropriate nitrile in a non-polar solvent, for example, cyclohexane.

Compounds of formula (IV) can also be prepared by reacting a compound of formula (XVIII) as hereinbefore defined with sodium sulphide (NaSH) or by metalation when L is halogen followed by reaction with sulpur.

Alternatively, compound of formula (IV) can be prepared from a compound of formula (XVIIIb)

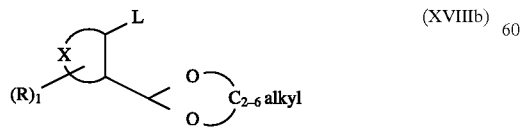 (XVIIIb)

wherein l, R, $R^2$, X and L are as hereinbefore defined and preferably $C_{2-6}$ alkyl is —$CH_2CH_2$— or —$CH_2$—$C(Me)_2$—$CH_2$—, by metalation of a compound of formula (XVIIIa) using, for example, magnesium or n-butyllithium followed by reaction with sulfur ($S_8$) and hydrolysis of the alkylenedioxy protecting group with, for example, acid.

Compounds of formula (XVIIIb) can be prepared from the corresponding compounds of formula (XVIII) by reaction with the appropriate $C_{2-6}$ diol, preferably 1,2-ethanediol or 2,2,-dimethyl-1,3-propanediol in a suitable solvent, for example toluene and preferably in the presence of a catalyst such as p-toluenesulfonic acid.

Compounds of formulae (V), (Va), (XIX), (XII), (VI) and $R^2CN$ as hereinbefore defined can be obtained commercially or prepared by methods known to those skilled in the art or obtainable from the chemical literature. Thus compounds of formula (V) can be prepared from the corresponding 2-substituted 2-aminoethanols, or from compounds of formula (Va) and compounds of formula (XII) from the corresponding 2-substituted-2amino-1,3-propanediols 2-substituted-2-aminoethanois and 2-substituted-2-amino-1, 3-propanediols can be obtained commercially or prepared by methods known to those skilled in the art or obtainable from the chemical literature.

Compounds of formula (I) wherein n=0 and $R^1$ is not hydrogen can be obtained by reacting the corresponding compound of formula (II) with, for example, an organometallic compound such as $R^1Li$, $R^1Cu$, $R^1Zn$, or $R^1MgBr$ wherein $R^1$ is as hereinbefore defined other than hydrogen.

Compounds of formula (I) wherein n=0 and $R^3$ is hydrogen can also be prepared by cyclising a compound of formula (VIII)

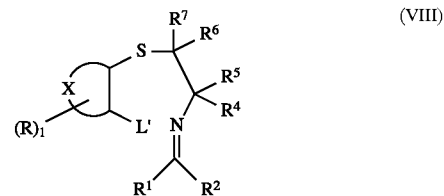 (VIII)

wherein l, R, $R^1$, $R^2$, $R^4$ to $R^7$ and X are as hereinbefore defined and L' is halogen, for example, bromine, by treatment with strong base, for example, n-butyl lithium, in a suitable solvent, such as THF, at a low temperature, for example, −78° C.

Compounds of formula (VIII) can be prepared by reaction of a compound of formula (IX)

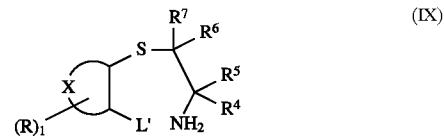 (IX)

wherein l, L', R, $R^4$ to $R^7$ and X are as hereinbefore defined, with a compound of formula $R^1R^2C$=O wherein $R^1$ and $R^2$ are as hereinbefore defined. The reaction is typically carried out in a non-polar solvent, for example, toluene, in the presence of an acid, such as p-toluenesulphonic acid.

Compounds of formula (IX) can be prepared by reacting a compound of formula (XI)

 (XI)

wherein l, L', R and X are as hereinbefore defined, with a compound of formula (V) wherein $R^4$ to $R^7$ are as hereinbefore defined, typically in a polar solvent, such as methanol.

Compounds of formula (IX) can also be prepared by reacting a compound of formula (XI) as hereinbefore defined with a compound of formula (XVII)

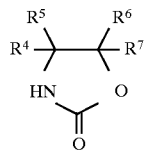
(XII)

wherein $R^4$ to $R^7$ are as hereinbefore defined, in the presence of a Lewis acid, for example, lithium chloride, at an elevated temperature, such as 170°–210° C.

Compounds of formulae $R^1R^2C=O$ as hereinbefore defined, (XI) and (XVII) can be obtained commercially or prepared by methods known to those skilled in the art or obtainable from the chemical literature. Thus compounds of formula (XI) may be prepared from the corresponding disulphides and compounds of formula (XVII) from the corresponding 2-substituted 2-aminoethanols.

Compounds of formula (I) wherein n=0 and $R^1$ and $R^3$ are both hydrogen can also be obtained by reacting a compound of formula (XIII)

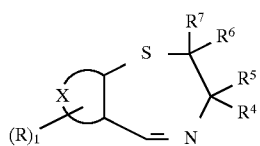
(XIII)

wherein l, R, $R^4$ to $R^7$ and X are as hereinbefore defined, using, for example, an organometallic compound, such as $R^2Li$, $R^2Cu$, $R^2Zn$, or $R^2MgBr$ wherein $R^2$ is as hereinbefore defined.

Compounds of formula (XIII) can be prepared by dehydrogenating the corresponding compound of formula (XIV)

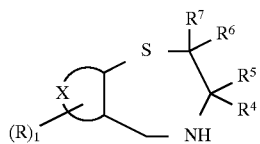
(XIV)

wherein l, R, $R^4$ to $R^7$ and X are as hereinbefore defined, using, for example, an oxidising agent, such as 2,3-dichloro-5,6-dicyano-1,4-benzoquinone (DDQ), in a suitable solvent, such as toluene, or preferably $KM_nO_4$ in a suitable solvent, such as t-butanol/$H_2O$.

Alternatively, compounds of formula (XIII) can be prepared by reacting a compound of formula (IV) wherein $R^2$ is hydrogen with a compound of formula (V) or (Va).

Compounds of formula (XIV) can be prepared by reducing the amide carbonyl group of the corresponding compound of formula (XV)

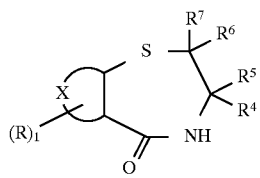
(XV)

wherein l, R, $R^4$ to $R^7$ and X are as hereinbefore defined using, for example, lithium aluminium hydride.

Compounds of formula (XV) can be prepared by reacting a compound of formula (XVI)

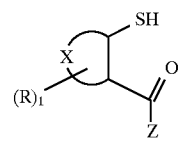
(XVI)

wherein l, R and X are as hereinbefore defined and Z is $C_{1-4}$ alkoxy, for example, methoxy, with a compound of formula (V) or (Va) wherein $R^4$ to $R^7$ are as hereinbefore defined.

The compound of formula (XVI) wherein X is benzo can be prepared from a suitably $(R)_l$ substituted 2,2'-dithiosalicylic acid or when l=0 from commercially available 2,2'-dithiosalicyclic acid by methods known to those skilled in the art. Compounds of formula (XVI) wherein l is not 0 can be obtained commercially or prepared by methods known to those skilled in the art or obtainable from the chemical literature.

Alternatively compounds of formula (I) wherein n=0 and $R^3$ is hydrogen can be prepared by cyclising a compound of formula (XXIX)

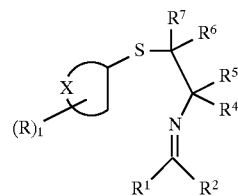
(XXIX)

wherein l, X, $R^1$, $R^2$, and $R^4$ to $R^7$ are as hereinbefore defined by reaction with a non-nucleophilic base such as LDA, which can then be reacted with oxone to give compounds of formula (I) wherein n=2.

Compounds of formula (XXIX) can be prepared from compounds of formula (XXX)

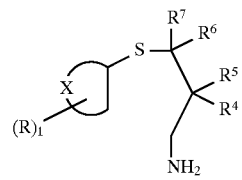
(XXX)

wherein l, X, and $R^4$ to $R^7$ are as hereinbefore defined, by reaction with $R^2CHO$ wherein $R^2$ is as hereinbefore defined.

Compounds of formula (XXX) can be prepared by reaction of compound of formula (V) with compounds of formula (VI).

Compounds of formula (I) can also be prepared starting from compounds of formula (XXI)

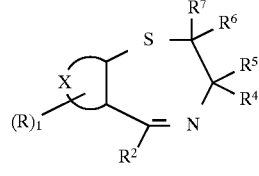
(XXI)

wherein X, l, R, $R^2$ and $R^5$ to $R^7$ are as hereinbefore defined, by steps well known in the art.

Compounds of formula (XXI) can be prepared by following methods described herein which methods will be obvious to one skilled in the art.

Compounds of formula (I) can also be prepared by reaction of compounds of formula (II) wherein $R^4=CH_2OH$ by oxidation of the alcohol with, for example, $SO_3$ pyridine in $Et_3N$/DMSO.

Compounds of formula (I) wherein $R^3$=OH, $C_{1-6}$ alkoxy or —O $C_{1-6}$ acyl can be prepared from compounds of formula (I) wherein $R^3$ is hydrogen by oxidation of the nitrogen with, for example, oxone® (potassium peroxyminosulphate) in methanol/water optionally followed by reactions known in the art.

Compounds of formula (I) wherein X=pyrrolo can be prepared from compounds of formula (XXVI)

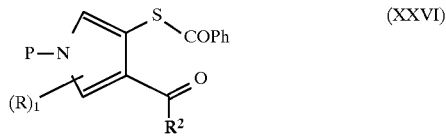

wherein P is a protecting group such as tri-isopropylsilyl, and R, l and $R^2$ are as hereinbefore defined, by refluxing with NaOH followed by reaction with a compound of formula (V) or (Va) in a suitable solvent such as methanol. The resulting compound (XXVII)

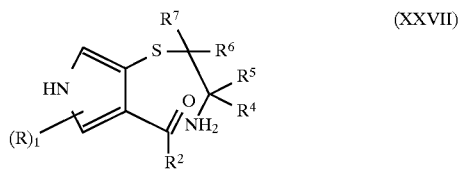

wherein $R^2$, $R^4$, $R^5$, $R^6$ and $R^7$ are as hereinbefore defined, is then reacted with for example lutidine/TSOH to give a compounds of formula (II) wherein l=0 and X is pyrrolo. These compounds can then be converted into compounds of formula (I) as previously described or by reaction with 1) $BH_3$/THF and 2) N-methyl morpholine-N-oxide, $O_sO_4$/tBuOH/THF at room temperature.

Compounds of formula (XXVI) can be prepared from compounds of formula (XXVIa)

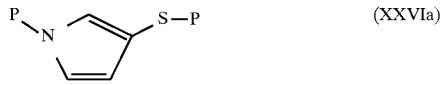

wherein P is as defined hereinbefore and can be the same or different, by reacting a compound of formula (XXVIa) with suitable acid halide compound, such as $R^2COCl$, wherein $R^2$ is as hereinbefore define, by a Friedel-Crafts reaction using, for example, aluminum chloride.

The compounds of formula (XXVIa) can be prepared by first reacting pyrrole with a strong base, for example n-butyllithium in an aprotic solvent such as THF, followed by N-protection with, for example TIPS-Cl (tri-isopropylsilyl chloride). The resulting N-protected pyrrole is halogenated with, for example N-bromosuccinimide (NBS), followed by metalation with, for example t-butyllithium and reaction with sulphur ($S_8$). The resulting sulphur compound is further S-protected with, for example, TIPS-Cl.

Compounds of formula (I) wherein X=pyrridyl can be prepared from compounds of formula (XVIII) wherein X=pyrridyl by reaction with for example, NaSH/DMSO and a compound of formula (V) or (Va). The resulting compound of formula (III) wherein X is pyrridyl, and R, l, $R^2$, and $R^4$ to $R^7$ are as hereinbefore defined can be converted to a compound of formula (II) wherein X=pyrridyl as previously described. These compounds of formula (II) can then be converted to compounds of formula (I) as previously described herein.

Compounds of formula (I) wherein $R^4$ is, for example, —$CH_2CH$=$CHCH_3$, can be hydrochlorinated using, for example, gaseous hydrogen chloride, to give the corresponding compound of formula (I) wherein $R^4$ is —$CH_2CHClCH_2CH_3$. Other functional group conversions will be readily apparent to one skilled in the art, for example the compound of formula (I) wherein $R^4$ is —$CH_2CHClCH_2CH_3$ can be hydrolysed using, for example basic $H_2O_2$, to give the corresponding compound of formula (I) wherein $R^4$ is —$CH_2CH(OH)CH_2CH_3$. This alcohol can be oxidized to the corresponding ketone by known methods for example $SO_3$/pyridine and $Et_3N$ in DMSO. Compounds of formula (I) wherein $R^4$ is, for example, —$CH_2CH_2COCH_3$ can be prepared by reducing and hydroxylating a compound of formula (I) wherein $R^4$ is $C_{2-6}$ alkenyl using, for example diborane followed by acidification and subsequent oxidation with basic $H_2O_2$. The resulting hydroxy compound can then be oxidized to the corresponding ketone by know methods, for example $SO_3$/pyridine and $Et_3N$ in DMSO. Alternatively, the compound of formula (II) wherein $R^4$ is —CHO can be alkenylated using a wittig reagent having an alkyl ketone and n-butyllithium to give the corresponding compound of formula (II) wherein $R^4$ is $C_{2-6}$ alkenyl substituted by OXO, followed by reduction of the alkene by methods described herein or known to one skilled in the art or available in the literature.

Compounds of formula (I) wherein n=0 and $R^3$ is not hydrogen can be prepared by N-alkylation of the corresponding compound of formula (II) with an alkyl halide, such as methyl iodide, in a polar solvent, for example, acetonitrile, prior to reduction to the compound of formula (I).

Compounds of formula (I) wherein n=1 or 2 can be prepared by oxidation of the corresponding compound of formula (I) wherein n=0 or by oxidation of the corresponding compound of formula (III) wherein n=0 prior to cyclisation and reduction to the compound of formula (I) using suitable oxidation conditions, for example, in the case where n is to be 2.30% aqu. $H_2O_2$ in the presence of trifluoroacetic acid.

Individual optical isomers of compounds of formula (I) substantially free, of other optical isomers can be obtained either by chiral synthesis, for example, by the use of the appropriate chiral starting material(s), such as the aziridine (V), or by resolution of the products obtained from achiral syntheses, for example, by chiral hplc.

Optional conversion of a compound of formula (I) to a corresponding acid addition salt may be effected by reaction with a solution of the appropriate acid, for example, one of those recited earlier. Optional conversion to a corresponding base salt may be effected by reaction with a solution of the appropriate base, for example, sodium hydroxide. Optional conversion to a physiologically functional derivative, such as an ester, can be carried out by methods known to those skilled in the art or obtainable from the chemical literature.

For a better understanding of the invention, the following Examples are given by way of illustration and are not to be construed in any way as limiting the scope of the invention.

SYNTHETIC EXAMPLE 1

I. Preparation of (−)-(RR)-3-butyl-3-ethyl-2,3,4,5-tetrahydro-5-phenyl-1,4-benzothiazepine 1,1-dioxide (a) Ethyl 2-aminobutyrate hydrochloride A slurry of 2-aminobutyric acid (100 g, Aldrich) in absolute ethanol (300 ml) was stirred under nitrogen at 0° C. and thionyl chloride (120.8 g) was added dropwise. The reaction was stirred overnight at 0° C. and then gradually warmed to room temperature. The resulting white slurry was heated under reflux for 3 hours, left to cool for 10 minutes, then poured into chilled diethyl ether (600 ml) with hand stirring. The suspension was filtered and the solid product dried to give the desired product (150 g) as a white solid. $^1$H NMR consistent with proposed structure.

(b) Ethyl 2-benzylideneaminobutyrate

A solution of the product from step (a) (149.6 g), magnesium sulphate (74.3 g), and triethylamine (246 ml) in dichloromethane (1500 ml) was stirred at room temperature under nitrogen and benzaldehyde (94.9 g, Aldrich) was added dropwise. The mixture was stirred at room temperature for 3 hours then filtered. The filtrate was concentrated, triturated in diethyl ether, filtered and concentrated to yield the desired product as a yellow oil (174 g). $^1$H NMR consistent with the proposed structure.

(c) (±)-Ethyl 2-benzylideneamino-2-ethylhexanoate

Sodium hydride (32.5 g, 60% dispersion in oil) and N,N-dimethylformamide (DMF) (700 ml) were stirred under nitrogen at room temperature and a solution of the product from (b) (178.1 g) in DMF was added dropwise. After 2 hours stirring at room temperature, a solution of butyl iodide (149.5 g) in DMF was added dropwise and the reaction left stirring for a further 2 hours. The reaction was poured into an ice cold mixture of water (560 ml), diethyl ether (300 ml) and ammonium chloride (120 g). The resulting organic layer was dried over potassium carbonate then concentrated to give the desired product as a brown oil (220 g).

(d) (±)-Ethyl 2-amino-2-ethylhexanoate

The product from (c) (233.0 g) was partitioned between petroleum ether and 10% w/w hydrochloric acid (421 ml) and stirred at room temperature for 2 hours. The aqueous layer was extracted twice with petroleum ether and then chilled with ethyl acetate in an ice-salt bath. Sodium hydroxide pellets were added to the mixture until the aqueous layer was at pH 10. The latter was extracted twice with ethyl acetate and the combined ethyl acetate layers were dried over potassium carbonate, then concentrated and vacuum distilled to give the desired product as a colourless oil. $^1$H NMR consistent with the proposed structure.

(e) (±)-2-Amino-2-ethylhexan-1-ol

Lithium aluminium hydride (22.2 g) was added to anhydrous diethyl ether (450 ml) under nitrogen. The product from (d) (129.0 g) was diluted with diethyl ether (40 ml) and added dropwise. The reaction was refluxed for 1 hour then cooled to room temperature. 1M sodium hydroxide (23 ml) was added dropwise followed by deionised water. The resulting suspension was filtered and the filtrate concentrated to give the desired product as a colourless oil (87.9 g). $^1$H NMR consistent with the proposed structure.

(f) (±)-2-Butyl-2-ethylaziridine

Acetonitrile (150 ml) and the product from (e) (20.0 g) were mixed under nitrogen, cooled to 2°–3° C. and chlorosulphonic acid (16.0 g, Aldrich) was added dropwise keeping the temperature below 10° C. The coolant was removed and the slurry left to stir for 80 minutes at room temperature. The reaction was concentrated in vacuo and co-distilled with water (50 ml). 50% Aqueous sodium hydroxide (55.2 g) and water (50 ml) were added and the mixture was distilled at atomspheric pressure. The organic layer was collected from the distillate and dried with solid potassium hydroxide to give the desired product (12.8 g). $^1$H NMR consistent with proposed structure.

(g) 2-Thiobenzophenone

A solution of N,N,N',N'-tetramethylethylenediamine (TMEDA) (104.6 g) in cyclohexane (500 ml) was cooled and 2.5M n-butyl lithium (360 ml) was added. A solution of thiophenol (50.0 g) in cyclohexane (100 ml) was added slowly to the butyl lithium solution and the reaction was stirred at room temperature overnight. Benzonitrile (46.4 g, Aldrich) in cyclohexane (100 ml) was added to give a slurry which was stirred overnight at room temperature. Water (500 ml) was added and the mixture stirred for 30 minutes then the aqueous layer was separated and treated with solid sodium hydroxide to give pH 14. The solution was boiled for 90 minutes, cooled to room temperature and acidified to pH 1–2 with conc. HCl. The acidic solution was extracted with dichloromethane and the combined extracts dried, then concentrated to give a red oil. The oil was treated with 1M aqu. NaOH, extracted with dichloromethane and the aqueous layer separated and treated with conc. HCl acid to give an oil. The oil was extracted into dichloromethane and the combined extracts dried, then concentrated to give the desired product as an orange-red oil (83.4 g). $^1$H NMR consistent with proposed structure.

(h) (±)-2-(2-Amino-2-ethylhexylthio)benzophenone

The product from (g) was dissolved in methanol (to a total volume of 250 ml) and an equimolar amount of the product from (f) in methanol (total volume 120 ml) was added over 20 minutes. The mixture was stirred at room temperature for 75 minutes then concentrated in vacuo to give a dark red oil. This oil was taken up in diethyl ether (400 ml) and filtered to remove contaminating solids. The desired product was left as a solution in ether for use in (i). $^1$H NMR consistent with proposed structure.

(i) (±)-3-Butyl-3-ethyl-5-phenyl-2,3-dihydrobenzothiazepine

1M Ethereal hydrochloric acid (275 ml) was added to a solution of the product from (h) (85.0 g) in diethyl ether and the mixture was concentrated in vacuo. The residue was azeotropically distilled by addition of 2,6-lutidine (175 ml) and refluxing in a Dean-Stark apparatus overnight. The mixture was concentrated in vacuo, neutralised by addition of 5% sodium bicarbonate then the minimum volume of ethyl acetate was added to dissolve the red oil. The organic layer was separated, washed with brine, dried and concentrated. The crude residue was purified by column chromatography on silica using toluene as eluant. Concentration of the relevant fractions gave the desired product (63.7 g) of an orange oil. $^1$H NMR consistent with the proposed structure.

(j) (±)-Trans-3-Butyl-3-ethyl-2,3,4,5-tetrahydro-5-phenyl-1,4-benzothiazepine

1M Diborane (211 ml in THF) was added over 45 minutes to a solution of the product from (i) (63.7 g) in THF under nitrogen. Reaction was stirred at room temperature for 17 hours. 50% Hydrochloric acid (125 ml) was added and the mixture was concentrated in vacuo. The residue was partitioned between aqu. NaOH and ethyl acetate. The organic layer was separated, dried and concentrated to give an orange-yellow oil (67.5 g) comprising cis and trans isomers which was chromatographed on silica using toluene as eluant to give the desired product as a pale yellow oil (27.3 g). $^1$H NMR consistent with the proposed structure.

(k) (±)-Trans-3-Butyl-3-ethyl-2,3,4,5-terrahydro-5-phenyl-1,4-benzothiazepine 1,1-dioxide 30% Aqueous hydrogen peroxide (73.1 g) and trifluoroacetic acid (TFA) (225 ml) were cooled and a solution of the product from (j) (70.0 g) in TFA (200 ml) was added. The reaction was stirred at room temperature for 24 hours, then added to water (1000 ml) and basified with solid sodium hydroxide. The resulting insoluble solid was filtered off, warmed with 1M aqu. NaOH and extracted into ethyl acetate. The combined extracts were evaporated in vacuo to give the desired product (69.0 g). $^1$H NMR consistent with the proposed structure.

(l) (−)-(RR)-3-Butyl-3-ethyl-2,3,4,5-tetrahydro-5-phenyl-1,4-benzothiazepine 1,1-dioxide The product from (k) (208.3 g) was mixed with diethyl ether (1500 ml) and (−)-di-p-toluoyl-L-tartaric acid (225.2 g, Schweitzerhall) in diethyl ether added. On standing, a white solid precipitated which was filtered off and recrystallised from acetone/hexane to give the desired product as the acid salt. The title compound was liberated from its salt by treatment with 1M aqu. NaOH and extracted with ethyl acetate. The combined extracts were evaporated in vacuo to give the desired product as a white solid (83.0 g), mp 115°–116° C.

Analysis: Calcd. C 70.55; H 7.61; N 3.92; S 8.97 Found: C 70.58; H 7.56; N 3.96; S 8.88

$^1$H NMR (DMSO-d$_6$), δ: 0.81–0.92 (6H, m, 2×CH$_3$); 1.15–1.40 (4H, m, 2×CH$_2$); 1.47–1.70 (3H, m, CH$_2$+NH); 1.80–1.90 (1H, m, CH$_2$); 2.13–2.24 (1H, m, CH$_2$); 3.07–3.46 (2H, q, CH$_2$SO$_2$); 6.09(1H, s, CHPh); 6.71–6.74 (1H, m, ArH); 7.26–7.41 (7H, m, ArH); 8.10–8.13 (1H, m, ArH)

SYNTHETIC EXAMPLE 2

Preparation of (±)-trans-3-((E)-2-butenyl)-3-ethyl-2,3,4,5-tetrahydro-5-phenyl-1,4-benzothiazepine 1,1-dioxide (a) (±)-2-(2-Butenyl)-2-ethylaziridine Using crotyl bromide in place of butyl iodide in step (c) of Synthetic Example 1, the title compound was prepared in an analagous manner to give a colorless oil. $^1$H NMR consistent with the proposed structure.

(b) 3-Ethyl-3-(2-butenyl)-5-phenyl-2,3-dihydrobenzothiazepine

This compound was prepared following the procedure of Synthetic Example 1(i), using the products from Synthetic Example 2(a) (9.0 g) and Synthetic Example 1(g) (15.0), but replacing ethereal HCL with conc. HCl (6 ml). Chromatography on silica using hexanes/EtOAc(9:1) as eluant afforded the title product as an orange oil (19.8 g). $^1$H NMR consistent with the proposed structure.

(c) (±)-Trans-3-((E)-2-butenyl)-3-ethyl-2,3,4,5-tetrahydro-5-phenyl-1,4-benzothiazepine Sodium borohydride (16.4 g, Aldrich) was added to the product from step (b) (19.8 g) in 250 ml 95% EtOH and stirred at room temperature for 17 hr. 6N HCl (200 ml) was added, stirred for 30 min and concentrated in vacuo. Deionized water (200 ml) was added to the residue, followed by 50% NaOH until basic to litmus paper. The mixture was extracted with EtOAc. The organic layer was separated, dried and concentrated to give an orange oil. Chromatography on silica using hexanes/EtOAc (98:2) as eluant gave the desired product as a beige solid (4.1 g), mp 69°–74° C. $^1$H NMR consistent with the desired structure.

(d) (±)-Trans-3-((E)-2-butenyl)-3-ethyl-2,3,4,5-tetrahydro-5-phenyl-1,4-benzothiazepine 1,1-dioxide Alumina (12 g, activity grade I, type WB-2, basic, Sigma) was added in portions to Oxone(22.9 g, Aldrich) and the product from step (c) (4.0 g) in 50 ml CH$_2$Cl$_2$. The reaction mixture was stirred at gentle reflux for 3 hr then at room temperature for 17 hr. The mixture was filtered and the filtrate was washed with 5% NaHCO$_3$. The organic layer was separated, dried and concentrated to give an orange oil. Chromatography on silica using hexanes/EtOAc (3:2) as eluant afforded the title product as tan solid (0.65 g), mp 167°–169° C.

Analysis: Calcd. C 70.95; H 7.09; N 3.94; S 9.02 Found: C 70.72; H 7.13; N 3.88; S 8.98

$^1$H NMR (DMSO-d$_6$), δ: 0.83(3H, t, CH$_3$); 1.40–1.48(5H, m, CH$_3$+CH$_2$); 2.60–2.67(3H, m, NH+CH$_2$); 3.35(4H, q, CH$_2$SO$_2$); 5.22–5.46(2H, m, CH═CH); 6.02(1H, d, CHPh); 6.56–6.59(1H, m, ArH); 7.28–7.50(7H, m, ArH); 7.95–7.99 (1H, m, ArH)

SYNTHETIC EXAMPLE 3

Preparation of (±)-trans-3-ethyl-2,3,4,5-tetrahydro-3-(3-methoxypropyl)-5-phenyl-1,4-benzothiazepine 1,1-dioxide (a) (±)-2-Allyl-2-ethylaziridine Using allyl bromide in place of butyl iodide in step (c) of Synthetic Example 1, the title compound was prepared in an analagous manner to give a colorless oil. $^1$H NMR was consistent with the proposed structure.

(b) (±)-3-Allyl-3-ethyl-5-phenyl-2,3-dihydrobenzothiazepine

This compound was prepared following the procedure of Synthetic Example 1(i), using the products from step (a) (27.8 g) and Synthetic Example 1(g) 57.8 g), but replacing ethereal HCl with conc. HCl (23 ml). Chromatography on silica using toluene as the eluant afforded the desired product as an orange oil (57.3 g). $^1$H NMR consistent with the proposed structure.

(c) (±)-Trans-3-(3-ethyl-2,3,4,5-tetrahydro-5-phenyl-1,4-benzothiazepin-3-yl)propanol A 1.0M solution of diborane in THF (185 ml, Aldrich) was added to a solution of the product from step (b) (57.3 g) in 300 ml of THF and stirred at room temperature for 17 hr. 6N HCl (200 ml) was added ana the mixture was concentrated in vacuo to remove THF. 1N NaOH and EtOAc were added to the aqueous phase and the organic layer was separated, dried and concentrated in vacuo. The residue was taken up in THF (400 ml) and 3N NaOH(310 ml) followed by 30% H$_2$O$_2$ (105.4 g) were added. The mixture was stirred at room temperature for 4 hr, then saturated NaCO$_3$ (200 ml) was added. The organic phase was separated, dried and concentrated in vacuo to get solids. Trituration of the solids with diethyl ether gave the title product as a white solid (30.8 g), mp 134°–135° C. $^1$H NMR consistent with the proposed structure.

(d) (±)-Trans-3-ethyl-2,3,4,5-tetrahydro-3-(3-methoxypropyl)-5-phenyl-1,4-benzothiazepine A 1.0M solution of potassium t-butoxide in THF (7.8 ml, Aldrich) was added to a solution of methyl iodide (1.1 g) and the product from step (c) (2.5 g) in 100 ml of THF. The reaction was stirred for 3 hr at room temperature, added deionized water and NaCl. The organic layer was separated, dried and concentrated in vacuo. Chromatography on silica using hexanes/EtOAc (85:15) as eluant afforded the desired product as a light yellow oil (2.0 g). $^1$H NMR consistent with the proposed structure.

(e) (±)-Trans-3-ethyl-2,3,4,5-tetrahydro-3-(3-methoxypropyl)-5-phenyl-1,4-benzothiazepine 1,1-dioxide This compound was prepared following the procedure of Synthetic Example 1(k), using the product from step (d) (2.0 g) to give the desired product as a white solid (1.9 g), mp 129°–130° C.

Analysis: Calcd. C 67.53; H 7.29; N 3.75; S 8.59 Found: C 67.41; H 7.31; N 3.78; S 8.64

$^1$H NMR (DMSO-d$_6$), δ: 0.80(3H, t, 3H); 1.24–1.54(4H, m, 2×CH$_2$); 1.67–1.77(1H, m, CH$_2$); 2.12–2.22(1H, m, CH$_2$); 2.67(1H, d, NH); 3.08(3H, s, OCH$_3$); 3.12–3.21(2H, m, CH$_2$); 3.38(2H, q, CH$_2$SO$_2$); 5.97(1H, d, CHPh); 6.53–6.57(1H, m, ArH); 7.28–7.49(7H, m, ArH); 7.94–7.98 (1H, m, ArH)

SYNTHETIC EXAMPLE 4

Preparation of (±)-trans-1-(3-ethyl-2,3,4,5-tetrahydro-5-phenyl-1,4-benzothiazepin-3-yl)-2-butanone S,S-dioxide (a) (±)-Trans-3-ethyl-2,3,4,5-tetrahydro-3-(2-hydroxybutyl)-5-phenyl-1,4-benizothiazepine This compound was prepared following the procedure of Synthetic Example 3(c), using the product from Synthetic Example 2(b) (11.6 g). Chromatography on silica using hexanes/EtOAc (4:1) as eluant afforded the desired product as an orange oil (8.0 g). $^1$H NMR consistent with the proposed structure.

(b) (±)-Trans-1-(3-ethyl-2,3,4,5-tetrahydro-5-phenyl-1,4-benzothiazepin-3-yl)-2-butanone Triethylamine (7.4 g, Aldrich) was added to a solution of the product from step (a) (8.3 g) dissolved in 40 ml of DMSO. The reaction mixture was chilled to 8°–10° C. and sulfur trioxide pyridine complex (11.6 g, Aldrich) was added over a period of 10 minutes. The reaction mixture was stirred for 4 hr, allowing bath to come to room temperature, then added to 700 ml of brine. The mixture was extracted with $CH_2Cl_2$ which was separated, dried and concentrated to give a pinkish oil. Chromatography on silica using hexanes/EtOAc (7:3) as eluant gave the title compound as a beige solid (2.1 g), mp 93°–96° C. $^1$H NMR consistent with the proposed structure.

(c) (±)-Trans-1-(3-ethyl-2,3,4,5-tetrahydro-5-phenyl-1,4-benzothiazepin-3-yl)-2-butanone S,S-dioxide This compound was prepared following the procedure of Synthetic Example 1(k), using the product from step (b) (2.05 g). Chromatography on silica using hexanes/EtOAc (4;1) as eluant afforded the desired product as a white solid(1.3 g), mp 110°–113° C.

Analysis: Calcd. C 67.89; H 6.78; N 3.77; S 8.63 Found: C 67.82; H 6.82; N 3.76; S 8.70

$^1$H NMR (DMSO-d$_6$), δ: 0.77–0.83(6H, m, $CH_3$); 1.45–1.57(1H, m, $CH_2$); 1.61–1.71(1H, m, $CH_2$); 2.40(2H, q, $CH_2$), 2.93(1H, s, NH); 3.34–3.41(2H, m, $CH_2$); 3.59(2H, q, $CH_2SO_2$); 6.02(1H, d, CHPh); 6.54–6.59(1H, m, ArH); 7.93–7.99(1H, m, ArH)

SYNTHETIC EXAMPLE 5

Preparation of (±)-trans-1-(3-ethyl-2,3,4,5-tetrahydro-8-methoxy-5-phenyl-1,4-benzothiazepin-3-yl)-2-butanone S,S-dioxide hydrochloride 1,1 hydrate (a) O-(2-benzoyl-5-methoxyphenyl)dimethylthiocarbamate Sodium hydride (8.8 g, Aldrich) was added slowly to a solution of 2-hydroxy -4-methoxybenzophenone (50.0 g, Aldrich) in 300 ml of dimethylformamide. Hexamethylphosphoramide (43.0 g) was then added dropwise and stirred at room temperature for 2 hours. Dimethylthiocarbamoyl chloride (37.0 g, Aldrich) was added and stirred overnight at 50° C. The reaction mixture was poured into deionized water (300 mL) and extracted with a petroleum ether/chloroform (1:4) mixture. The organic layer was washed with 10% sodium hydroxide, brine and concentrated to give the title product as a yellow solid (40.0 g), mp 94°–96° C. $^1$H NMR was consistent with proposed structure.

(b) S-(2-Benzoyl-5-methoxyphenyl)dimethylthiocarbamate

The product (40.0 g) from step (a) was suspended in phenyl ether(300 mL) and heated to an internal temperature of 262° C. for 30 minutes. After cooling to room temperature, the reaction mixture was chromatographed on silica using hexane, then hexanes/ethyl acetate (7:3) as eluants to afford the title product as a yellow-brown solid (30.0 g), mp 96°–98° C. $^1$H NMR was consistent with proposed structure.

(c) 2-Mercapto-4-methoxybenzophenone

Potassium hydroxide pellets (20.0 g) was slowly added to a solution of the product (28.0 g) from step (b) dissolved in 800 ml methanol/tetrahydrofuran(1:1). After refluxing for 4 hours, the reaction was cooled to room temperature, methylene chloride was added and the solution was extracted with 5% hydrochloric acid. The organic layer was dried and concentrated. Chromatography on silica using hexanes/ethyl acetate (99:1) as the eluant afforded the title product as a yellow solid (17.1 g), mp 74°–76° C. $^1$H NMR consistent with proposed structure.

(d) (±)-3-But-2-enyl-3-ethyl-8-methoxy-5-phenyl-2,3-dihydrobenzothiazepine

This compound was prepared following the procedure of Synthetic Example 1(i), using the product from step (c) (32.0 g) and the product from Synthetic Example 2(a) (18.8 g), but replacing ethereal HCl with p-toluenesulphonic acid (200 mg). Chromatography on silica using hexanes/EtOAc (9:1) as eluant gave the desired product as an orange oil (35.7 g). $^1$H NMR consistent with the proposed structure.

(e) (±)-Trans-1-(3-ethyl-2,3,4,5-tetrahydro-8-methoxy-5-phenyl-1,4-benzothiazepin-3-yl)-2-butanol This compound was prepared following the procedure of Synthetic Example 3(c), using the product from step (d) (35.7 g). Chromatography on silica using hexanes/EtOAc (65:35) as eluant afforded the title product as an orange oil (27.7 g). $^1$H NMR consistent with the proposed structure.

(f) (±)-Trans-1-(3-ethyl-2,3,4,5-tetrahydro-8-methoxy-5-phenyl-1,4-benzothiazepin-3-yl)-2-butanol S,S-dioxide This compound was prepared following the procedure of Synthetic Example 1(k), using the product from step (e) (27.7 g) to give solids which were recrystallized from acetone to give the desired product as a white solid (12.3 g), mp 201°–202° C. $^1$H NMR consistent with the proposed structure.

(g) (±)-Trans-1-(3-ethyl-2,3,4,5-tetrahydro-8-methoxy-5-phenyl-1,4-benzothiazepin-3-yl)-2-butanone S,S-dioxide hydrochloride 1,1 hydrate This compound was prepared following the procedure of Synthetic Example 4(b), using the product from step (f) (9.0 g). Chromatography on silica using hexanes /EtOAc (3:1) as eluant gave a white foam which was treated with ethereal HCl to give the title product as a white solid (5.0 g), mp 134°–136° C.

Analysis: C 57.72; H 6.65; N 3.06; S 7.01 Found: C 57.72; H 6.66; N 3.06; S 7.12

$^1$H NMR (DMSO-d$_6$), δ: 0.85(3H, t, $CH_3$); 1.96(2H, broad s, $CH_2$); 2.47–2.59(3H, m, $CH_2$), 3.56–3.61(2H, m, $CH_2$); 3.80(3H, s, $OCH_3$); 4.32(1H, broad d, $CH_2$); 4.75–4.82(2h, broad s, $NH_2^+$); 6.25(1H, broad s, CHPh); 6.65(1H, d, ArH); 7.14–7.17(1H, m, ArH); 7.47–7.60(6H, m, ArH)

SYNTHETIC EXAMPLE 6

Preparation of (±)-trans-3-(1-butenyl)-3-ethyl-2,3,4,5-tetrahydro-5-phenyl-1,4-benzothiazepine 1,1-dioxide hydrochloride 0.4 hydrate (a) (±)-Trans-3-ethyl-2,3,4,5-tetrahydro-3-(2-hydroxybutyl)-5-phenyl-1,4-benzothiazepine 1,1-dioxide This compound was prepared following the procedure of Synthetic Example 1(k), using the product from Synthetic Example 4(a) (11.7 g). Chromatography on silica using hexanes/EtOAc (65:35) as eluant afforded the desired product as a white solid (5.8 g). $^1$H NMR consistent with the proposed structure.

(b) (±)-Trans-3-(1-butenyl)-3-ethyl-2,3,4,5-tetrahydro-5-phenyl-1,4-benzothiazepine 1,1-dioxide hydrochloride 0.4 hydrate Diethyl azodicarboxylate (2.1 g, Aldrich) was added to triphenylphosphine (3.1 g, Aldrich) and the product from step (a) (3.6 g) in 100 ml of THF. The reaction mixture was stirred at room temperature for 17 hr then concentrated in vacuo. Chromatography on silica using hexanes/EtOAc (7:3) as eluant gave a light yellow oil which was treated with ethereal HCl to give the title product as a beige solid (0.40 g), mp 190°–192° C.

Analysis: C 63.19; H 6.77; N 3.51; S 8.18 Found: C 63.17; H 6.75; N 3.51; S 8.09

$^1$H NMR (DMSO-d$_6$), δ: 0.75–0.87(6H, m, 2×CH$_3$); 1.41–1.58(2H, m, CH$_2$); 2.62–2.70(2H, m, CH$_2$); 3.19(1H, d, NH); 3.37(2H, q, CH$_2$SO$_2$); 5.26–5.43(2H, m, CH=CH); 6.02(1H, d, CHPh); 6.55–6.61(1H, m, ArH); 7.31–7.52(7H, m, ArH); 7.94–8.00(1H, m, ArH)

SYNTHETIC EXAMPLE 7

Preparation of (±)-trans-3-(ethoxyethyl)-3-ethyl-2,3,4,5-tetrahydro-5-phenyl-1,4-benzothiazepine 1,1-dioxide hydrochloride hemihydrate (a) (±)-4-Ethyl-4-(hydroxymethyl)-2-oxazolidinone Sodium methoxide (2.2 g, Aldrich) was added to a solution of 2-amino-2-ethyl-1,3-propanediol(100.0 g, Aldrich) and diethyl carbonate (169.0 g, Aldrich) This solution was refluxed in a Dean Stark apparatus until no more EtOH was collected. The reaction mixture was cooled, added acetone (200 ml) and allowed to stand overnite at room temperature. The resulting suspension was filtered to give 81.0 g of the desired product as a beige solid. $^1$H NMR consistent with the proposed structure.

(b) (±)-4-Ethyl-4-[(tosyloxy)methyl]-2-oxazolidinone

Tosyl chloride (142.2 g, Aldrich) was added to an ice-chilled solution of the product from step (a) (102.7 g) dissolved in pyridine (175 ml. Aldrich). The reaction mixture was stirred at ice bath temperature for six hours, then allowed to come to room temperature. The heterogeneous mixture was added to 1500 ml of a solution of brine and 1N HCl. stirred until solids appeared, filtered and washed with diethyl ether to give 194.6 g of a beige solid as the title product. $^1$H NMR consistent with the proposed structure.

(c) (±)-4-(((2-Benzoylphenyl)thio)methyl)-4-ethyl-2-oxazolidinone

2-Thiobenzophenone (125.3 g, Synthetic Example 1(g)) in 150 ml of DMF was added slowly to sodium hydride (60%, 23.4 g, Aldrich) in 175 ml of DMF. After complete addition, the product from step (b) (175.1 g), in 200 ml of DMF, was added in a steady stream to the reaction mixture. The reaction was stirred at 60° C. for 3 hr, cooled and added to 3L of brine to give solids. The reaction mixture was filtered and the solids were slurried in 250 ml of 95% EtOH and filtered to give the desired product as a beige solid (168.8 g), mp 103°–104° C. $^1$H NMR consistent with the proposed structure.

(d) (±)-2,3-Dihydro-3-ethyl-5-phenyl-1,4-benzothiazepine-3-methanol

The product from step (c) (168.8 g) was dissolved in 1200 ml EtOH/water (2:1) and 128.8 g of KOH was added and refluxed for 24 hrs. The reaction mixture was cooled and concentrated in vacuo then ethyl acetate and deionized water were added. The organic layer was separated and concentrated in vacuo to give 155.2 g of a red-orange oil. Chromatography on silica using hexanes/EtOAc (1:1) as eluant afforded the title product as a light orange oil (55.7 g). $^1$H NMR consistent with the proposed structure.

(e) (±)-3-Ethyl-2,3-dihydro-5-phenyl-1,4-benzothiazepine-3-carbaldehyde

Triethyl amine (56.7 g, Aldrich) was added to a solution of the product from step (d) (55.7 g) dissolved in 140 ml of DMSO. The reaction mixture was chilled to 8°–10° C. and sulfur trioxide pyridine complex (89.3 g, Aldrich) in 200 ml of DMSO was added over a period of 16 minutes. The reaction mixture was stirred for 5 hr, allowing bath temperature to come to room temperature, then added to 3L of brine. This mixture was extracted with ethyl acetate which was separated, dried and concentrated to give 56.0 g of a red oil. Hexane(200 ml) was added, allowed to stir until solids formed, and then filtered to give the desired product as a tan solid (43.1 g), mp 98°–100° C. $^1$H NMR consistent with the proposed structure.

(f) (±)-3-Ethyl-2,3-dihydro-5-phenyl-3-vinyl-1,4-benzothiazepine

A 1.0M solution of potassium t-butoxide in THF (82 ml, Aldrich) was added to a suspension of methyl triphenylphosphonium bromide (29.0 g, Aldrich) in 250 ml of THF. After complete addition, the reaction mixture was refluxed for one hour, cooled with an ice bath and the product from step (e) (12.0 g) in 70 ml of THF was added. The reaction was stirred for 1 hr at room temperature, refluxed for 2.5 hr and then stirred at room temperature for 17 hr. Saturated NH$_4$Cl(200 ml) was added, the organic layer was separated, dried and concentrated to give a red-orange oil. Chromatography on silica using hexanes/EtOAc (9:1) as eluant afforded the title product as a light orange oil (11.0 g). $^1$H NMR consistent with the proposed structure.

(g) (±)-Trans-3-ethyl-2,3,4,5-tetrahydro-1,4-benzothiazepine-3-ethanol

A 1.0M solution of diborane in THF (37.0 ml, Aldrich) was added to a solution of the product from step (f) (11.0 g) in 200 ml of THF and stirred for 17 hr at room temperature. 6N HCl (100 ml) was added and the mixture was concentrated in vacuo to remove THF. 1N NaOH and EtOAc were added to the aqueous phase and the organic layer was separated, dried and concentrated in vacuo. The residue was taken up in THF (200 ml) and 3N NaOH(62 ml) followed by 30% H$_2$O$_2$ (21.2 g) were added. The mixture was stirred at room temperature for 2.5 hr, then 125 ml of saturated Na$_2$CO$_3$ was added. The organic phase was separated, dried and concentrated in vacuo. The residue was chromatographed on silica using hexanes/EtOAc (7:3) as eluant to give the desired product as an oil (3.0 g). $^1$H NMR was consistent for the proposed structure.

(h) (±)-Trans-3-(ethoxyethyl)-3-ethyl-2,3,4,5-tetrahydro-5-phenyl-1,4-benzothiazepine A 1.0M solution of potassium t-butoxide in THF (11.0 ml, Aldrich) was added to a solution of ethyl iodide (1.7 g, Aldrich) and the product from step (g) (3.0 g) in 100 ml of THF. The reaction was stirred for 4 hr at room temperature, added deionized water and NaCl. The organic layer was separated, dried and concentrated to give an oil. Chromatography on silica using hexanes/EtOAc (7:3) as eluant afforded the desired product as an oil (1.6 g). $^1$H NMR consistent with the proposed structure.

(i) (±)-Trans-3-(ethoxyethyl)-3-ethyl-2,3,4,5-tetrahydro-5-phenyl-1,4-benzothiazepine 1,1-dioxide hydrochloride hemihydrate 30% H$_2$O$_2$ (1.6 g) and trifluoroacetic acid(TFA) (15 ml) were cooled and a solution of the product from step (h) (1.6 g) in TFA(15 ml) was added. The reaction was stirred at room temperature for 17 hr. then added to 300 ml of deionized water, basified with solid NaOH and warmed for 1 hr. The mixture was extracted with EtOAc which was separated, dried and concentrated to give an oil. Chromatography on silica using hexanes/EtOAc (3:2) as eluant gave a yellow oil which was treated with ethereal HCl to give the title product as a beige solid (0.95 g), mp 219°–220° C.

Analysis: Calcd. C 60.20; H 6.98; N 3.34: S 7.65 Found: C 60.19; H 6.78; N 3.33; S 7.76

$^1$H NMR of the free base(CDCl$_3$), δ: 0.92(3H, t, CH$_3$); 1.03(3H, t, CH$_3$); 1.48–1.65(3H, m, CH$_2$+NH); 2.11–2.18

(1H, m, CH$_2$); 2.57–2.62(1H, m, CH$_2$); 3.31(2H, q, CH$_2$SO$_2$); 3.26–3.48(4H, m, 2×CH$_2$); 6.14(1H, s, CHPh); 6.70–6.73(1H, m, ArH); 7.25–7.40(7H, m, ArH); 8.09–8.12 (1H, m, ArH)

SYNTHETIC EXAMPLE 8

Preparation of (±)-trans-3-(ethoxymethyl)-3-ethyl-2,3,4,5-tetrahydro-5-phenyl-1,4-benzothiazepine 1,1-dioxide hydrochloride (a) (±)-Trans-3-ethyl-2,3,4,5-tetrahydro-5-phenyl-1,4-benzothiazepine-3-methanol A 1.0M solution of diborane in THF (55.0 ml, Aldrich) was added to the product from Synthetic Example 7(d) (16.4 g) in 150 ml of THF. The reaction was stirred overnite at room temperature, then 100 ml of 6N HCl was added and THF was removed in vacuo. NaOH and EtOAc were added to the aqueous layer and the organic layer was separated, dried and concentrated. Chromatography on silica with hexanes/EtOAc (7:3) as eluant afforded the desired product as a white solid (4.0 g), mp 104°–106° C. $^1$H NMR consistent with the proposed structure.

(b) (±)Trans-3-(ethoxymethyl)-3-ethyl-2,3,4,5-tetrahydro-5-phenyl-1,4-benzothiazepine This compound was prepared following the procedure of Synthetic Example 7(h), using the product from step (a) (2.3 g) to give the title product as a yellow oil (2.0 g). $^1$H NMR consistent with the proposed structure.

(c) (±)Trans-3-(ethoxymethyl)-3-ethyl-2,3,4,5-tetrahydro-5-phenyl-1,4-benzothiazepine 1,1-dioxide hydrochloride This compound was prepared following the procedure of Synthetic Example 7(i), using the product from step (b) (1.0 g). Chromatography on silica using hexanes/EtOAc (7:3) as eluant afforded a yellow oil which was treated with ethereal HCl to give the desired product as a white solid (0.40 g), mp 194°–199° C.

Analysis: Calcd. C 60.67; H 6.62; N 3.54; S 8.10 Found: C 60.68; H 6.66; N 3.56; S 8.19

$^1$H NMR (DMSO-d$_6$), δ: 0.90(3H, t, CH$_3$); 1.00(3H, t, CH$_3$); 1.73–2.00(2H, m, CH$_2$); 3.47–3.90(6H, m, 3×CH$_2$); 4.80–5.70(2H, broad s, NH$_2^+$), 6.20(1H, s, CHPh); 6.82–6.84(1H, m, ArH); 7.54–7.64(7H, m, ArH); 8.05–8.08 (1H, m, ArH)

SYNTHETIC EXAMPLE 9

Preparation of (±)-trans-ethyl 3-(3-ethyl-2,3,4,5-tetrahydro-5-phenyl-1,4-benzothiazepin-3-yl) propionate 1,1-dioxide (a) (±)-2-((2-Amino-2-(hydroxymethyl)butyl)thio) benzophenone This compound was prepared following the procedure of Synthetic Example 7(d). It was isolated, as an oil, by silica chromatography as the major product of that reaction. $^1$H NMR consistent with the proposed structure.

(b) (±)-2-((2-Amino-2-(hydroxymethyl)butyl)sulfonyl) benzophenone

This compound was prepared following the procedure of Synthetic Example 7(i), using the product from step (b) (40.4 g) to give the title product as a white solid (38.7 g), mp 150°–151° C. $^1$H NMR consistent with the proposed structure.

(c) (±)-3-Ethyl-2,3-dihydro-5-phenyl-1,4-benzothiazepine-3-methanol 1,1-dioxide

The product from step (b) (38.7 g) was dissolved in 600 ml of 2,6-lutidine and 120 ml of 1.0M HCl in diethyl ether was then added. The reaction mixture was refluxed overnite, using a Dean Stark trap, then concentrated in vacuo. The residue was taken up in 5% NaHCO$_3$ whereupon solidification took place. The solids were filtered and washed with ether to afford the desired product as a light brown solid (25.7 g), mp 170°–171° C. $^1$H NMR consistent with the proposed structure.

(d) (±)-3-Ethyl-2,3-dihydro-5-phenyl-1,4-benzothiazepine-3-carbaldehyde 1,1-dioxide This compound was prepared following the procedure of Synthetic Example 7(e), using the product from step (c) (25.6 g). Chromatography on silica with hexanes/EtOAc (4:1) as eluant afforded the desired product as a white solid (21.0 g), mp 127°–128° C. $^1$H NMR consistent with the proposed structure.

(e) (±)-(E)-Ethyl 3-(2,3-dihydro-3-ethyl-5-phenyl-1,4-benzothiazepin-3-yl)acrylate 1,1-dioxide Triethylphosphonoacetate (14.5 g, Aldrich) in 40 ml of THF was added to 60% NaH(2.6 g, Aldrich) in 100 ml of THF. The mixture was stirred for 30 minutes at room temperature then the product from step (d) (21.0 g) in 60 ml of THF was added and stirred for 17 hr at room temperature. The reaction mixture was concentrated in vacuo and the residue was partitioned between CH$_2$Cl$_2$ and deionized water. The organic layer was separated, dried and concentrated to get solids which were recrystallized from MeOH/H$_2$O to give the title product as a tan solid (20.7 g), mp 158°–159° C. $^1$H NMR consistent with the proposed structure.

(f) (±)-Trans-ethyl 3-(3-ethyl-2,3,4,5-tetrahydro-5-phenyl-1,4-benzothiazepin-3-yl)propionate 1,1-dioxide The product from step (e) (10.2 g) was dissolved in 100 ml of EtOAc and 2.2 g of 10% Pd/C(Aldrich) was added, then placed on a Parr hydrogenator for 6 days. The reaction mixture was filtered and concentrated in vacuo to give an oil. Chromatography on silica using hexanes/EtOAc (7:3) as eluant afforded the desired product as a white solid (0.90 g), mp 147°–148° C.

Analysis: Calcd. C 65.81; H 6.78; N 3.49; S 7.99 Found: C 65.55; H 6.83; N 3.44; S 7.89

$^1$H NMR(CDCl$_3$), δ: 0.79(3H, t, CH$_3$); 1.08(3H, t, CH$_3$); 1.41–1.45(2H, m, CH$_2$); 1.89–2.15(3H, m, CH$_2$); 2.65–2.78 (1H, m, CH$_2$); 2.81(1H, s, NH); 3.43(2H, q, CH$_2$SO$_2$); 3.87–3.95 (2H, m, CH$_2$); 5.95(1H, d, CHPh); 6.53–6.56(1H, m, ArH); 7.29–7.48(7H, m, ArH); 7.96–7.99(1H, m, ArH)

SYNTHETIC EXAMPLE 10

Preparation of (±)-trans-(E)-4-(3-ethyl-2,3,4,5-tetrahydro-5-phenyl-1,4-benzothiazepin-3-yl)-3-buten-2-one 1,1-dioxide (a) (±)-Trans-3-ethyl-2,3,4,5-tetrahydro-5-phenyl-1,4-benzothiazepine-3-methanol 1,1-dioxide This compound was prepared following the procedure of Synthetic Example 7(i), using the product from Synthetic Example 8(a) (27.5 g) to give the title product as a beige solid (25.7 g), mp 134°–137° C. $^1$H NMR consistent with the proposed structure.

(b) (±)-Trans-3-ethyl-2,3,4,5-tetrahydro-5-phenyl-1,4-benzothiazepine-3-carbaldehyde 1,1-dioxide This compound was prepared following the procedure of Synthetic Example 7(e), using the product from step (a) (24.0 g ) to afford the title product as a beige solid (19.2 g), mp 125°–128° C. $^1$H NMR consistent with the proposed structure.

(c) (±)-Trans-(E)-4-(3-ethyl-2,3,4,5-tetrahydro-5-phenyl-1,4-benzothiazepin-3-yl)-3-buten-2-one 1,1-dioxide The product from step (b) (6.0 g) and 1-triphenylphosphoranylidene-2-propanone (6.4 g, Aldrich)

were added to 200 ml of toluene and refluxed for 17 hr. The reaction mixture was concentrated in vacuo and the solid residue was triturated with diethyl ether. The ether insoluble solid was chromatographed on silica using hexanes/EtOAc (3:2) as eluant to give the desired product as a beige solid (2.0 g), mp 196°–198° C.

Analysis: Calcd. C 68.26; H 6.27; N 3.79; S 8.68 Found: C 68.01; H 6.30; N 3.85; S 8.78

$^1$H NMR (DMSO-d$_6$), δ: 0.76(3H, t, CH$_3$); 1.51–1.67(2H, m, CH$_2$); 2.16(3H, s, CH$_3$CO); 3.19(1H, s, NH); 3.74(2H, q, CH$_2$SO$_2$); 5.93(1H, d, CHPh); 6.43(2H, q, CH=CH); 6.54–6.61(1H, m, ArH), 7.32–7.52(7H, m, ArH); 7.93–7.97 (1H, m, ArH)

SYNTHETIC EXAMPLE 11

Preparation of (±)-2,3,4,5-tetrahydro-8-methoxy-5-phenylspiro(1,4-benzothiazepine-3,1-cyclohexane) 1,1-dioxide (a) (1-Amino-1-cyclohexyl)methanol 1-Amino-1-cyclohexanecarboxylic acid(51.5 g, Aldrich) was added to 150 ml of THF followed by boron trifluoride etherate(27 ml, Aldrich). The reaction mixture was heated to 40° C., stirred for 10 minutes and then a 1.0M solution of diborane(380 ml, Aldrich) was added. The mixture was refluxed for 2 hr, cooled and added THF/water (1:1,25 ml) followed by 6N NaOH(95 ml). The reaction mixture was refluxed for 2 hr, cooled to room temperature and the organic layer was separated, washed with brine, dried and concentrated to give a light yellow oil (34.0 g). $^1$H NMR consistent with the proposed structure.

(b) Cyclohexanespiro-2'-aziridine

This compound was prepared following the procedure of Synthetic Example 1(f), using the product from step (a) (188.6 g) to give the title product (66.9 g) as a colorless oil. $^1$H NMR consistent with the proposed structure.

(c) 2,3-Dihydro-8-methoxy-5-phenyl-1,4-benzothiazepine-3-spirocyclohexane

This compound was prepared following the procedure of Synthetic Example 1(i), using the products firm step (b) (4.7 g) and Synthetic Example 5(c) (11.5 g), but replacing ethereal HCl with conc. HCl (4.3 ml). Chromatography on silica using hexanes/EtOAc (95:5) as eluant afforded the desired product as a yellow oil (12.5 g). $^1$H NMR consistent with the proposed structure.

(d) (±)-2,3,4,5-Tetrahydro-8-methoxy-5-phenylspiro(1,4-benzothiazepine-3,1-cyclohexane) 1,1-dioxide This compound was prepared following the procedure of Synthetic Example 1(j), using the product from step (c) (12.5 g) to give the title product as a white solid(12.2 g), mp 138°–139° C. $^1$H NMR consistent for the proposed structure.

(e) (±)-2,3,4,5-Tetrahydro-8-methoxy-5-phenylspiro(1,4-benzothiazepine-3,1-cyclohexane) 1,1-dioxide This compound was prepared following the procedure of Synthetic Example 1(k), using the product from step (d) (11.7 g) to afford the desired product as a white solid (10.0 g), mp 168°–170° C.

Analysis: C 67.90; H 6.78; N 3.77; S 8.63 Found: C 67.90; H 6.69; N 3.75; S 8.72

$^1$H NMR (DMSO-d$_6$), δ: 1.25–1.59(10H, m, CH$_2$); 2.46 (1H, d, NH); 3.39(2H, q, CH$_2$SO$_2$); 3.81(3H, s, OCH$_3$); 5.89(1H, d, CHPh); 6.49(1H, d, ArH); 7.06(1H, m, ArH); 7.32–7.49(6H, m, ArH)

SYNTHETIC EXAMPLE 12

Preparation of (±)-tans-3-butyl-3-ethyl-2,3,4,5-tetrahydro-5-(4-pyridyl)-1,4-benzothiazepine 1,1-dioxide (a) (±)-1-(((2-Bromophenyl)thio)methyl)-1-ethylpentanamine To a solution of 2-bromothiophenol (13.5 g, Lancaster) in methanol (45 ml) was added dropwise 2-butyl-2-ethylaziridine (10.0 g, Synthetic Example 1(f)). The mixture was stirred at room temperature for 1 hour. Solvent was evaporated to afford the title product as a light yellow oil (25.6 g). $^1$H NMR consistent with the proposed structure.

(b) (±)-N-((4-pyridyl)formylidene)-1-(((2-bromophenyl)thio)methyl)-1-ethylpentanamine A mixture of the product from step (a) (12.8 g), 4-pyridinecarboxaldehyde (343 ml, Aldrich), magnesium sulfate (21.5 g), and toluene (80 ml) was stirred at room temperature for 18 hours. The mixture was filtered and the solvent was evaporated to provide the title product as a light yellow oil (16.7 g). $^1$H NMR consistent with the proposed structure.

(c) (±)-Cis/trans-3-butyl-3-ethyl-2,3,4,5-tetrahydro-5-(4-pyridyl)-1,4-benzothiazepine A solution of the product from step (b) (16.7 g) in anhydrous tetrahydrofuran (125 ml) was cooled to −70° C. under N$_2$ and 2.5M n-butyl lithium (16 ml. Aldrich) in hexanes was added dropwise. The reaction mixture was stirred at −70° C. for 3 hours and quenched with 10% ammonium chloride (60 ml). The organic layer was separated and the aqueous layer was extracted twice with diethyl ether. The organic layers were combined, dried and concentrated. Chromatography on silica with hexanes/acetone (9:1) as eluant afforded the title product as a yellow oil (21.0 g). $^1$H NMR consistent with the proposed structure.

(d) (±)-Trans-3-butyl-3-ethyl-2,3,4,5-tetrahydro-5-(4-pyridyl)-1,4-benzothiazepine 1,1-dioxide A solution of the product from step (c) (4.8 g) was cooled to 0° C. and a solution of oxone (12.6 g, Aldrich) in water (60 ml) was added. The mixture was stirred at room temperature for 2.5 hours, diluted with water (200 ml), and neutralized with sodium bicarbonate. The mixture was extracted twice with chloroform. The organic layers were dried and concentrated. Chromatography on silica with hexanes/ethyl acetate (2:1) as eluant provided the title product as a white solid (2.0 g), mp 110°–111° C.

Analysis: Calcd: C, 67.01; H, 7.31; N, 7.81; S, 8.94 Found: C, 67.12; H, 7.32; N, 7.85; S, 8.97

$^1$H NMR (DMSO-d$_6$), δ: 0.75(3H, t, CH$_3$); 0.82(3H, t, CH$_3$); 1.00–1.22(4H, m, 2×CH$_2$); 1.40–1.50(2H, m, CH$_2$); 1.70–1.82(1H, m, CH$_2$); 1.97–2.10(1H, m, CH$_2$); 2.85(1H, d, NH); 3.41(2H, q, CH$_2$SO$_2$); 6.00(1H, d, CHPh); 6.50–6.60(1H, m, ArH); 7.45(2H, d, ArH); 7.50–7.60(2H, m, ArH); 7.95–8.05(1H, m, ArH); 8.62(2H, d, ArH).

SYNTHETIC EXAMPLE 13

(±)-Trans-3-butyl-3-ethyl-2,3,4,5-tetrahydro-4-hydroxy-5-(4-pyridyl)-1,4-benzothiazepine 1,1-dioxide The title compound was obtained as a by-product of Synthetic Example 12 step (d) as a white solid (0.15 g), mp 178°–179° C.

Analysis: Calcd: C, 64.14; H, 7.00; N, 7.48; S, 8.56 Found: C, 63.96; H, 7.09; N, 7.25; S, 8.42

$^1$H NMR (DMSO-d$_6$), 67 : 0.79(3H, t, CH$_3$); 0.81(3H, t, CH$_3$); 1.00–1.40(5H, m, CH$_2$); 1.55–1.65(1H, m, CH$_2$); 1.80(1H, broad t, CH$_2$); 2.05(1H, broad t, CH$_2$); 3.42CH$_2$SO$_2$); 6.39(1H, s, CHPh); 6.57–6.62(1H, m, ArH); 7.45–7.55(4H, m, ArH); 7.90–8.00(1H, m, ArH); 8.16(1H, s, NOH); 8.58–8.62(2H, m, ArH)

SYNTHETIC EXAMPLE 14

Preparation of (±)-trans-3-butyl-3-ethyl-2,3,4,5-tetrahydro-5-(2-thienyl)-1,4-benzothiazepine 1,1-dioxide (a) (±)-3-Butyl-3-ethyl-2,3-dihydro-1,4-benzothiazepin-5 (4H)-one To a solution of methyl thiosalicylate (25.0 g, Aldrich) in methanol (95 ml) at 0° C. was added 2-butyl-2-ethylaziridine (20.0 g, Synthetic Example 1(f)) and the mixture was stirred at room temperature for 18 hours. Solvent was evaporated and toluene (200 ml) and sodium methoxide (8.2 g) were added. The mixture was heated to reflux for 4.5 hours, removing water through a Dean-Stark trap. Solvent was evaporated and the residue was partitioned between 5% HCl (500 ml) and dichloromethane (400 ml). The organic layer was separated, dried and concentrated. Crystallization from hexanes/ethyl acetate provided the title compound as a white solid (38.0 g), mp 92°–93° C. $^1$H NMR consistent with the proposed structure.

(b) (±)-3-Butyl-3-ethyl-2,3,4,5-tetrahydro-1,4-benzothiazepine

A solution of the product from step (a) (46.5 g.) in tetrahydrofuran (260 ml) was cooled to 0° C., and 1M diborane (450 ml, Aldrich) in THF was slowly added. The resulting mixture was heated to reflux for 48 hours, cooled to 0° C., and treated carefully with 6M aqueous HCl. The mixture was heated to reflux for 1.5 hours, concentrated to 400 ml and extracted twice with diethyl ether. The organic layers were dried and concentrated to afford the title product (44.0 g) as a colorless oil. $^1$H NMR consistent with the proposed structure.

(c) (±)-3-Butyl-3-ethyl-2,3-dihydro-1,4-benzothiazepine

To a solution of the product from step (b) (6.0 g) in tert-butyl alcohol (180 ml) was added a solution of potassium permangante (5.7 g) in water (90 ml). The mixture was heated to reflux for 10 minutes, cooled to room temperature, and filtered through celite. Solvent was evaporated to provide the title compound (5.9 g) as a colorless oil. $^1$H NMR consistent with the proposed structure.

(d) (±)-Cis/Trans-3-Butyl-3-ethyl-2,3,4,5-tetrahydro-5-(2-thienyl)-1,4-benzothiazepine A solution of the product from step (c) (6.0 g) in anhydrous THF (150 ml) was cooled to 0° C. under N$_2$ and boron trifluoride etherate (3.75 ml) was added. The mixture was stirred at 0° C. for 1 hour, cooled to –700° C., treated with 1M 2-thienyl lithium (90 ml. Aldrich) in tetrahydrofuran, allowed to warm to room temperature, and quenched with 10% ammonium chloride (60 ml). The organic layer was separated and the aqueous layer was extracted twice with diethyl ether. The organic layers were combined, dried and concentrated. Chromatography on silica with hexanes/ethyl acetate (99:1) as eluant afforded the title compound (6.2 g) as a greenish oil. $^1$H NMR consistent with the proposed structure.

(e) (±)-Trans-3-butyl-3-ethyl-2,3,4,5-tetrahydro-5-(2-thienyl)-1,4-benzothiazepine 1,1-dioxide This compound was prepared following the procedure of Synthetic Example 12(d), using the product from step (d) (5.0 g). Chromatography on silica with hexanes/ethyl acetate (9:1) as eluant provided the title compound as a white solid (1.5 g). mp 93°–95° C.

Analysis: Calcd: C, 62.78; H. 6.93; N, 3.85; S, 17.64
Found: C, 62.83; H. 6.96; N, 3.91; S, 17.56

$^1$H NMR (DMSO-d$_6$), δ: 0.75–0.82(6H, m, 2×CH$_3$); 1.15–1.27(4H, m, 2×CH$_2$); 1.32–1.45(2H, m, CH$_2$); 1.80–2.00(2H, m, CH$_2$); 2.83(1H, d, NH); 3.31(2H, q, CH$_2$SO$_2$); 6.22(1H, d, CHPh); 6.93(1H, d, ArH); 7.06–7.10 (1H, m, ArH); 7.40–7.60(3H, m, ArH); 7.96(1H, d, ArH).

SYNTHETIC EXAMPLE 15

Preparation of (±)-trans-3-butyl-3-ethyl-2,3,4,5-tetrahydro-5-(1H-pyrrol-1-yl)-1,4-benzothiazepine 1,1-dioxide (a) (±)-Cis/trans-3-butyl-3-ethyl-2,3,4,5-tetrahydro-5-(1H-pyrrol-1-yl)-1,4-benzothiazepine This compound was prepared following the procedure of Synthetic Example 16(d) using 1M 1-pyrolyllithium (58 ml, Aldrich) and the product from Synthetic Example 5(d) (4.75 g) to afford the title compound (2.4 g) as a a greenish oil. $^1$H NMR consistent with the proposed structure.

(b) (±)-Trans-3-butyl-3-ethyl-2,3,4,5-tetrahydro-5-(1H-pyrrol-1-yl)-1,4-benzothiazepine 1,1-dioxide To a solution of the product from step (a) (2.1 g) in THF/tert-butyl alcohol (42 ml, 4:1) was added N-methylmorpholine N-oxide (7.9 g, Aldrich) and 2.5% osmium tetroxide (17 ml, Aldrich) in tert-butyl alcohol. The mixture was heated to reflux for 2 hours and treated with saturated sodium bisulfite. The mixture was extracted with diethyl ether, dried, and concentrated. Chromatography on silica with hexanes/ethyl acetate (19:1) provided the title product (0.5 g) as a white solid foam; m.p. 50°–52° C.

Analysis: Calcd: C, 65.86; H. 7.56; N, 8.08; S. 9.25
Found: C. 65.87; H, 7.51; N, 8.04; S, 9.32

$^1$H NMR (DMSO-d$_6$), δ: 0.75–0.85(6H, m, 2×CH$_3$); 1.10–1.30(4H, m, 2×CH$_2$); 1.40–1.53(2H, m, CH$_2$); 1.80–1.90(1H, m, CH$_2$); 1.92–2.00(1H, m, CH$_2$); 3.45(2H, q, CH$_2$SO$_2$); 3.50(1H, d, NH); 5.99(1H, d, ArH); 6.10(2H, s, ArH); 6.70(1H, d, CHPh); 6.95(2H, s, ArH); 7.45–7.55 (2H, m, ArH); 7.95(1H, d, ArH)

SYNTHETIC EXAMPLE 16

Preparation of (±)-Trans-3-butyl-3-ethyl-2,3,4,5-tetrahydro-5-phenylpyrido(4,3-F)-1,4-benzothiazepine 1,1-dioxide (a) Alpha-(3-chloro-4-pyridyl)benzyl alcohol A solution of lithium diisopropylamide was prepared under nitrogen atmosphere by combining in tetrahydrofuran diisopropylamine (50.6 g) and 2.5M n-butyl lithium(200 ml) in hexanes at −78° C. 3-Chloropyrimidine (50 g) was added slowly to the stirred reaction while maintaining the temperature below −70° C. After 15 minutes benzaldehyde (53 g) was added while maintaining temperature below −60° C. After 24 hours the reaction was quenched with water, extracted with ether, washed with water and concentrated. The residue was triturated with ethyl acetate-hexane (1:4), filtered and the resulting tan powder was rinsed with diethyl ether-hexane mixture to give a tan powder (52 g), mp 139°–141° C. $^1$H NMR is consistent with proposed structure.

(b) 3-Chloro-4-pyridyl phenyl ketone

Pyridinium chlorochromate (109.7 g) was added to a 1 liter dichloromethane solution of the product from a larger run of step (a) (111.85 g). The reaction was allowed to stand overnight (initially exothermic) and then filtered through Florisil and decolorizing carbon and evaporated to afford an off-white solid (76.8 g), mp. 49°–51° C. $^1$H NMR is consistent with proposed structure.

(c) (±)-3-((2-Amino-2-ethylhexyl)thio)-4-pyridyl phenyl ketone

A mixture of the product from step (b) (4.3 g), 2-butyl-2-ethylaziridine (2.54 g, Synthetic Example 1(f)), and sodium hydrogen sulfide hydrate (1.48 g) in dimethylsulfoxide was stirred 48 hours at ambient temperature. The reaction mixture was diluted with diethyl ether and washed with aqueous sodium hydroxide, dried, filtered and evaporated to a yellow viscous oil. The oil was chromatographed on silica gel using ethyl acetate-ethanol (3:1) as eluant to give a yellow viscous oil (1.87 g). $^1$H NMR is consistent with proposed structure.

(d) (±)-3-Butyl-3-ethyl-2,3-dihydro-5-phenylpyrido(4,3-F)-1,4-benzothiazepine

The product from step (c) (1.27 g) was treated in accordance with step (i) of Example 1 to produce 0.95 g of a yellow oil. $^1$H NMR is consistent with proposed structure.

(e) (±)-Trans-3-butyl-3-ethyl-2,3,4,5-tetrahydro-5-phenylpyrido(4,3-F)-1,4-benzothiazepine A larger sample of the product from step (d) (12.08 g) was treated in accordance with step (j) of Example 1 to produce 1.82 g of a colorless oil. $^1$H NMR is consistent with proposed structure.

(f) (±)-Trans-3-butyl-3-ethyl-2,3,4,5-tetrahydro-5-phenylpyrido(4,3-F)-1,4-benzothiazepine 1,1-dioxide The product from step (e) (0.87 g) was treated in accordance with step (k) of Example 1 to produce 0.28 g of a white solid, mp 114°–116° C.

Analysis: Calcd. C 67.01; H 7.31; N 7.81; S 8.94 Found: C 66.95; H 7.38; N 7.78; S 8.86

$^1$H NMR (DMSO-d$_6$), δ: 0.73 (3H, t); 0.80 (3H, t); 0.9–1.3 (4H, m); 1.5 (2H, m); 1.7 (1H, m); 2.0 (1H, m); 2.90 (1H, d); 3.28 (1H, d); 3.75 (1H, d); 5.84 (1H, d); 7.4 (5H, m); 8.62 (1H, d); 8.98 (1H, s)

SYNTHETIC EXAMPLE 17

Preparation of (±)-Trans-3-butyl-3-ethyl-3,4,5,7-tetrahydro-5-phenyl-2H-pyrrolo(3,4-F)-1,4-benzothiazepine 1,1-dioxide 0.1 hydrate (a) 1-(Triisopropylsilyl)pyrrole To a solution of pyrrole (33.54 g) in THF (700 ml) at −78° C. under nitrogen was added a solution of 2.5M n-butyl lithium(200 ml) in hexane. After one hour triisopropylsilyl chloride (98 g) was added. After 24 hours the reaction was diluted with diethyl ether, washed with water, dried over sodium sulfate, filtered and evaporated to a tan oil which was distilled at 115°–119° C. (0.2 mm Hg) to give 102.6 g of a colorless mobile liquid. $^1$H NMR is consistent with proposed structure.

(b) 1,3-Bis(trisisopropylsilyl)-1H-pyrrole

The product from step (a) (102.6 g) was dissolved in tetrahydrofuran (600 ml) and treated with N-bromosuccinimide (89 g) at −78° C. under nitrogen for 15 minutes. The reaction was allowed to come to ambient temperature over one hour, concentrated, diluted with hexane, filtered and the solvent removed. The residue was dissolved in tetrahydrofuran (600 ml), cooled to −78° C., and tert-butyl lithium in pentane (588 ml 1.7M) was added. After one hour elemental sulfur (16 g) was added and the mixture was stirred for one hour at ambient temperature. The reaction was cooled to −78° C. and triisopropyl silyl chloride (98 g) was added and the reaction was allowed to warm to room temperature. After 24 hrs the solvent was removed under reduced pressure and the residue in diethyl ether was washed with water, dried over sodium sulfate, filtered, concentrated and distilled at 160°–205° C. (0.2 mm) to give a colorless viscous oil (119.8 g). $^1$H NMR is consistent with proposed structure.

(c) 3-Benzoyl-4-(benzoylthio)-1-(triisopropylsilyl)pyrrole

Aluminum chloride (2.31 g), benzoyl chloride (2.46 g), and the product from step (b) (3.6 g) were combined in dichloromethane (30 ml) under nitrogen at −78° C. After one hour the reaction was mixed with saturated aqueous sodium bicarbonate and the organic layer was dried over sodium sulfate, filtered and concentrated. The residue was triturated with hexane and filtered to give a rose pink solid (1.90 g), mp 120°–122° C. $^1$H NMR is consistent with proposed structure.

(d) (±)-3-Benzoyl-4-((2-amino-2-ethylhexyl)thio)-1H-pyrrole

A mixture of the product from step (c) (24.9 g), 250 ml methanol and 106 ml 1N sodium hydroxide was warmed to reflux for 10 minutes then 1N hydrochloric acid (53 ml) was added followed by 2-butyl-2-ethylaziridine (7.7 g, Synthetic Example 1(f)). After one hour the reaction was diluted with ethyl acetate and washed with 1N sodium hydroxide and then water. The organic layer was dried, filtered and concentrated. The residue was chromatographed on silica gel eluting with ethyl acetate-ethanol (3:1) to give a tan viscous oil (15.32 g). $^1$H NMR is consistent with proposed structure.

(e) (±)-3-Butyl-3-ethyl-2,3-dihydro-5-phenyl-7H-pyrrolo(3,4-F)-1,4-benzothiazepine A larger sample of the product from step (d) (16.46 g) was used in accordance with step (i) of Example 1 to produce the desired compound as a tan powder (1.15 g), mp 145°–146° C.

(f) (±)-Trans-3-butyl-3-ethyl-3,4,5,7-tetrahydro-5-phenyl-2H-pyrrolo(3,4-F)-1,4-benzothiazepine A larger sample of the product from step (e) (9.75 g) was treated in analogy with step (j) of Example 1 to produce the desired product as a tan solid (1.5 g), mp 41°–43° C.

(g) (±)-Trans-3-butyl-3-ethyl-3,4,5,7-tetrahydro-5phenyl-2H-pyrrolo(3,4-F)-1,4-benzothiazepine 1,1-dioxide 0.1 hydrate The product of step (f) (0.57 g) was dissolved in 15 ml of a tert-butanol-tetrahydrofuran (1:5) solution and treated with 4-methyl morpholine-N-oxide (0.57 g) and 1 ml of a 2.5% by weight solution of osmium tetroxide in tert-butanol. After stirring at ambient temperature overnight, the reaction was diluted with ethyl acetate and washed three times with saturated aqueous sodium metabisulfite and once with water. The organic layer was dried over sodium sulfate, filtered through Florisil and concentrated to a golden viscous oil that solidified to give a tan solid (0.55 g), mp 127°–129° C.

Analysis: Calcd. C 65.52; H 7.58; N 8.04; S 9.21 Found: C 65.61; H 7.80; N 7.73; S 8.91

$^1$H NMR (DMSO-d$_6$), δ: 0.70 (3H, t); 0.87 (3H, t); 1.0–1.3 (4H, m); 1.3–1.6 (2H, m); 1.7 (1H, m); 2.0 (1H, m); 2.21 (1H, d); 3.17 (1H, d); 3.39 (1H, d); 5.10 (1H, d); 5.70 (1H, s); 7.2–7.5 (6H, m); 11.25 (1H, sb)

SYNTHETIC EXAMPLE 18

Preparation of (±)-trans-3-butyl-3-ethyl-2,3,4,5-tetrahydro-5-phenylthieno(2,3-F)-1,4-benzothiazepine 1,1-dioxide (a) (−)-3-((2-Amino-2-ethylhexyl)thio)thiophene To a solution of n-butyl lithium in hexane (194 ml 1.6M) under nitrogen at −78° C. was added diethyl ether(120 ml) and then dropwise 3-bromothiophene (28 ml). The reaction was warmed to −30° C. and then cooled to −50° C. and powdered sulfur (10 g) was added. The reaction was stirred 15 hours at room temperature and then a solution of potassium hydroxide (24 g) in 160 ml water was added and the ether layer was discarded. The aqueous layer was treated at −5° C. with 6N hydrochloric acid (125 ml) and extracted with dichloromethane and the extract was dried over magnesium sulfate. Filtration and solvent removal afforded crude 3-thiophenthiol (14.1 g). The crude 3-thiophenthiol (10 g) was combined with 2-butyl-2-ethylaziridine (12.6 g, Synthetic Example 1(f)) at 0° C. and the reaction was stirred 15 hours at room temperature. The crude reaction product was purified by column chromatography on silica using 5% methanol in diethyl ether as eluant to give the desired product as an oil (16.4 g). $^1$H NMR is consistent with proposed structure.

(b) (±)-Trans-3-butyl-3-ethyl-2,3,4,5-tetrahydro-5-phenylthieno(2,3-F)-1,4-benzothazepine A mixture of the product from step (a) (15 g), magnesium sulfate (5 g), triethylamine (1 ml), and dichloromethane (40ml) was stirred at room temperature under nitrogen and benzaldehyde (6.1 g) was added dropwise. The mixture was stirred at room temperature for 60 hours then filtered. The filtrate was concentrated, diluted with petroleum ether, filtered and concentrated to yield the intermediate benzylidene as an oil (18.5 g). $^1$H NMR is consistent with the proposed structure. The intermediate benzylidene (5 g) in THF (15 ml) was added dropwise under nitrogen to lithium diisopropylamide (8 ml, 2M) at −78° C. After 15 minutes the reaction was warmed to room temperature for 30 minutes and then cooled to −78° C. and saturated ammonium chloride (30 ml) was added. The reaction was partitioned between water and diethyl ether and the organic phase was dried over sodium sulfate, filtered and evaporated to 5 g of an oil. Column chromatography on silica gel eluting with toluene gave 1.3 g of the cis isomer followed by the desired compound as a solid (2.8 g). $^1$H NMR is consistent with the proposed structure.

(c) (±)-Trans-3-butyl-3-ethyl-2,3,4,5-tetrahydro-5-penylthieno(2,3-F)-1,4-benzothiazepine 1,1-dioxide A solution of the product from step (b) (2.5 g) in methanol (50 ml) and dichloromethane (15 ml) was cooled in an ice bath and treated with a solution of Oxone (9.2 g) in water (60 ml) and the reaction was allowed to stir 24 hours at room temperature. The reaction was diluted with saturated sodium bicarbonate (100 ml), extracted with chloroform and the organic extracts were dried over sodium sulfate. Solvent was removed under reduced pressure and the residue was purified by column chromatography on silica gel eluting with ethyl acetate-petroleum ether (1:9). The product was crystallized from ethyl acetate and petroleum ether affording the desired compound as an off-white solid (0.65 g), mp 123°–125° C.

Analysis: Calcd. C 62.77; H 6.93; N 3.85; S 17.64 Found: C 62.82; H 6.95; N 3.85; S 17.64

$^1$H NMR (DMSO-d$_6$), δ: 0.78 (3H, t); 0.82 (3H, t); 1.1 (2H, m); 1.2 (2H, m); 1.5 (2H, m); 1.8 (2H, m); 2.94 (1H, d); 3.36 (1H, d); 3.74 (1H, d); 5.56 (1H, d); 7.3–7.5 (7H, m)

SYNTHETIC EXAMPLE 19

Preparation of (±)-trans-3-ethyl-2,3,4,5-tetrahydro-5-phenyl-3-(4,4,4-trifluorobutyl)-1,4-benzothiazepine 1,1-dioxide The title compound was prepared following the procedures of Synthetic Example 1(a)–(j), but using 1-bromo-4,4,4-trifluorobutane in step (c). The product was a mixture of cis and trans isomers. Fractional recrystallization gave the title compound, a solid, mp 107°–123° C. (0.5 g) which contained 33% of the cis-isomer.

Analysis: Calcd.: C 61.30; H 5.88; N 3.40; S 7.79; Found: C 63.00; H 6.79; N 3.50; S 8.01

$^1$H NMR (DMSO-d$_6$), δ: 0.76 (0.9H, t, CH$_3$); 0.85 (2.1H, t, CH$_3$); 1.35–1.53 (4H, m); 1.80 (1H, m); 2.21 (3H, m); 2.81 (1H, t); 3.21 (1H, dd); 3.70 (1H, dd); 5.99 (1H, d, CHPh); 6.62 (1H, m, ArH); 7.29 (1H, m, ArH); 7.37 (4H, m, ArH); 7.45 (2H, m, ArH); 8.01 (1H, m, ArH). The peak at δ: 0.76 (0.9H, t, CH$_3$) is associated with the cis-isomer, the peak at δ: 0.85 (2.1H, t, CH$_3$) is associated with the title compound.

Each of the following compounds of formula (I) was prepared by a method analogous to one of the synthetic routes described above. In all cases, $^1$H NMR and elemental analysis were consistent with the proposed structure.

SYNTHETIC EXAMPLE 20–78

20) (±)-2,3,4,5-Tetrahydro-5-phenylspiro(1,4-benzothiazepine-3,1'-cyclohexane) 1,1-dioxide, mp 177°–179° C.;

21) (±)-Trans-2,3,4,5-tetrahydro-3-isopropyl-3-methyl-5-phenyl-1,4-benzothiazepine 1,1-dioxide 0.25 H$_2$O, mp 130°–132° C.;

22) (+)-(S)-2,3,4,5-Tetrahydro-5-phenylspiro(1,4-benzothiazepine-3,1'-cyclohexane) 1,1-dioxide, mp 210°–211° C.;

23) (−)-(R)-2,3,4,5-Tetrahydro-5-phenylspiro(1,4-benzothiazepine-3,1'-cyclohexane) 1,1-dioxide, mp 210°–211° C.;

24) (±)-Trans-2,3,4,5-tetrahydro-3-isopropyl-3-methyl-5-phenyl-1,4-benzothiazepine hydrochloride, mp 211°–213° C.;

25) (±)-Cis-2,3,4,5-tetrahydro-3-isopropyl-3-methyl-5-phenyl-1,4-benzothiazepine hydrochloride, mp 268°–270° C.;

26) (±)-3-sec-Butyl-2,3,4,5-tetrahydro-3-methyl-5-phenyl-1,4-benzothiazepine hydrochloride, mp 202°–205° C.;

27) (±)-4,5-Dihydro-5-phenylspiro(1,4-benzothiazepine-3-(2H),1'-cyclopentane)hydrochloride 0.25 H$_2$O, mp 224°–226° C.;

28) (±)-2,3,4,5-Tetrahydro-5-phenylspiro(1,4-benzothiazepine-3,1'-cyclohexane)hydrochloride H$_2$O, mp 167°–169° C. (eff.);

29) (±)-5-(2-Fluorophenyl)-2,3,4,5-tetrahydrospiro(1,4-benzothiazepine-3,1'-cyclohexane) 1,1-dioxide, mp 160°–161° C.;

30) (±)-Cis-3-(2,3,4,5-tetrahydro-3-methyl-5-phenyl-1,4-benzothiazepin-3-yl)propionic acid 1,1-dioxide 0.5 H$_2$O, mp 132°–133° C.;

31) (±)-Trans-Ethyl 3-(2,3,4,5)-tetrahydro-3-methyl-5-phenyl-1,4-benzothiazepin-3-yl)propionate 1,1-dioxide, mp 143°–148° C.;

32) (±)-Cis-Ethyl 5-(2,3,4,5-tetrahydro-3-methyl-5-phenyl-1,4-benzothiazepin-3-yl)valerate 1,1-dioxide, mp 121°–122° C.;

33) (±)-Trans-3-((E)-2-Butenyl)-3-ethyl-2,3,4,5-tetrahydro-5-phenyl-1,4-benzothiazepine, mp 69°–74° C.;

34) (−)-Trans-3-Ethyl-2,3,4,5-tetrahydro-3-isopropyl-5-phenyl-1,4-benzothiazepine 1,1-dioxide, mp 116°–118° C.;

35) (±)-Cis-3-iso-Butyl-3-ethyl-2,3,4,5-tetrahydro-5-phenyl-1,4-benzothiazepine 1-oxide, mp 91°–93° C.;

36) (±)-Cis-3-iso-Butyl-3-ethyl-2,3,4,5-tetrahydro-5-phenyl-1,4-benzothiazepine 1,1-dioxide, mp 149°–151° C.;

37) (±)-Trans-3-iso-Butyl-3-ethyl-2,3,4,5-tetrahydro-5-phenyl-1,4-benzothiazepine 1-oxide, mp 92°–93° C.;

38) (±)-Trans-3-iso-Butyl-3-ethyl-2,3,4,5-tetrahydro-5-phenyl-1,4-benzothiazepine 1,1-dioxide mp 101°–103° C.;

39) (±)-Cis-3-Butyl-3-ethyl-2,3,4,5-tetrahydro-5-(3-pyridyl)-1,4-benzothiazepine 1,1-dioxide, mp 60°–61° C.;

40) (±)-Cis-Ethyl-2,3,4,5-tetrahydro-5-phenyl-1,4-benzothiazepine-3-carbaldehyde 1,1-dioxide, mp 162°–164° C.;

41) (±)-Cis-2,3,4,5-Tetrahydro-3-isopropyl-3-methyl-5-phenyl-1,4-benzothiazepine 1,1-dioxide 0.66 H$_2$O, mp 119°–120° C.;

42) (±)-Trans-3-Ethyl-2,3,4,5-tetrahydro-3-isopropyl-5-phenyl-1,4-benzothiazepine 1,1-dioxide, mp 121°–124° C.;

43) (±)-Cis-3-Ethyl-2,3,4,5-tetrahydro-3-isopropyl-5-phenyl-1,4-benzothiazepine 1,1-dioxide, mp 150°–152° C.;

44) (±)-Cis-3-Butyl-3-ethyl-2,3,4,5-tetrahydro-4-hydroxy-5-(3-pyridyl)-1,4-benzothiazepine 1,1-dioxide, mp 202°–205° C.;

45) (±)-Trans-3-(3-Ethyl-2,3,4,5-tetrahydro-5-phenyl-1,4-benzothiazepin-3-yl)propanol 1,1-dioxide, mp 164°–165° C.;
46) (±)-Trans-3-Ethyl-5-(4-Fluorophenyl)-2,3,4,5-tetrahydro-7-methoxy-3-(3-methoxypropyl)-1,4-benzothiazepine 1,1-dioxide hydrochloride, mp 179°–181° C.;
47) (±)-Cis-3-Butyl-3-ethyl-2,3,4,5-tetrahydro-5-phenylpyrido(4,3-F)-1,4-thiazepine 1,1-dioxide 0.333 H$_2$O, mp 111°–112° C.;
48) (±)-Cis-3-Butyl-3-ethyl-2,3,4,5-tetrahydro-5-(1H-pyrrol-1-yl)-1,4-benzothiazepine 1,1-dioxide, mp 50°–52° C.;
49) (±)-Cis-3-Butyl-3-ethyl-2,3,4,5-tetrahydro-5-phenyl-7H-pyrrolo(3,4-F)-1,4-thiazepine 1,1-dioxide 0.125 H$_2$O, mp 75°–77° C.;
50) (±)-2,3,4,5-Tetrahydro-7-methoxy-5-phenylspiro(1,4-benzothiazepine-3,1-cyclohexane) 1,1-dioxide, mp 142°–143° C.;
51) (±)-Trans-1-(3-Ethyl-2,3,4,5-tetrahydro-7-methoxy-5-phenyl-1,4-benzothiazepin-3-yl)-2-butanone S,S-dioxide hydrochloride, mp 175°–176° C.;
52) (±)-Trans-3-butyl-3-ethyl-2,3,4,5-tetrahydro-5-phenylnaphtho(3,2-F)-1,4-benzothiazepine 1,1-dioxide, mp 128°–131° C.;
53) (±)-Trans-3-Butyl-3-ethyl-2,3,4,5-tetrahydro-5-(2-pyridyl)-1,4-benzothiazepine 1,1-dioxide, mp 50°–53° C.;
54) (±)-Trans-3-Butyl-3-ethyl-2,3,4,5-tetrahydro-5-(3-pyridyl)-1,4-benzothiazepine 1,1-dioxide 0.25 hydrate, mp 153°–155° C.;
55) (±)-Trans-1-(3-Ethyl-2,3,4,5-tetrahydro-7,8-dimethoxy-5-phenyl-1,4-benzothiazepin-3-yl)-2-butanone S,S-dioxide, mp 142°–146° C.;
56) (±)-Trans-3-(1-butenyl)-3-ethyl-2,3,4,5-tetrahydro-8-methoxy-5-phenyl-1,4-benzothiazepine 1,1-dioxide
57) (±)-Trans-3-(1-butenyl)-3-ethyl-2,3,4,5-tetrahydro-7,8-dimethoxy-5-phenyl-1,4-benzothiazepine 1,1-dioxide
58) (±)-Trans-1-(3-Ethyl-2,3,4,5-tetrahydro-8-methoxy-5-phenyl-1,4-benzothiazepin-3-yl)-3-butanone S,S-dioxide
59) (±)-Trans-1-(3-Ethyl-2,3,4,5-tetrahydro-7,8-dimethoxy-5-phenyl-1,4-benzothiazepin-3-yl)-3-butanone S,S-dioxide
60) (±)-Trans-1-(3-Ethyl-2,3,4,5-tetrahydro-8-methoxy-5-phenyl-1,4-benzothiazepin-3-yl)-1-butanone S,S-dioxide
61) (±)-Trans-1-(3-Ethyl-2,3,4,5-tetrahydro-7,8-dimethoxy-5-phenyl-1,4-benzothiazepin-3-yl)-1-butanone S,S-dioxide
62) (±)-Trans-1-(3-ethyl-2,3,4,5-tetrahydro-8-methoxy-5-phenyl-1,4-benzothiazepin-3-yl)-4,4,4-trifluoro-1-butanone S,S-dioxide
63) (±)-Trans-1-(3-ethyl-2,3,4,5-tetrahydro-7,8-dimethoxy-5-phenyl-1,4-benzothiazepin-3-yl)-4,4,4-trifluoro-1-butanone S,S-dioxide
64) (±)-Trans-1-(3-ethyl-2,3,4,5-tetrahydro-7,8-dimethoxy-5-phenyl-1,4-benzothiazepin-3-yl)-3,3,4,4,4-pentafluoro-2-butanone S,S-dioxide
65) (±)-Trans-1-(3-ethyl-2,3,4,5-tetrahydro-8-methoxy-5-phenyl-1,4-benzothiazepin-3-yl)-3,3,4,4,4-pentafluoro-2-butanone S,S-dioxide
66) (±)-Trans-1-(3-ethyl-2,3,4,5-tetrahydro-7,8-dimethoxy-5-phenyl-1,4-benzothiazepin-3-yl)-4,4,4-trifluoro-2-butanone S,S-dioxide
67) (±)-Trans-1-(3-ethyl-2,3,4,5-tetrahydro-8-methoxy-5-phenyl-1,4-benzothiazepin-3-yl)-4,4,4-trifluoro-2-butanone S,S-dioxide
68) (±)-Trans-3-ethyl-2,3,4,5-tetrahydro-8-methoxy-5-phenyl-3-(4,4,4-trifluorobutyl)-1,4-benzothiazepine 1,1-dioxide
69) (±)-Trans-3-ethyl-2,3,4,5-tetrahydro-7,8-dimethoxy-5-phenyl-3-(4,4,4-trifluorobutyl)-1,4-benzothiazepine 1,1-dioxide
70) (±)-Trans-1-(3-(2,2,2-trifluoroethyl)-2,3,4,5-tetrahydro-8-methoxy-5-phenyl-1,4-benzothiazepin-3-yl)-2-butanone S,S-dioxide
71) (±)-Trans-1-(3-(2,2,2-trifluoroethyl)-2,3,4,5-tetrahydro-7,8-dimethoxy-5-phenyl-1,4-benzothiazepin-3-yl)-2-butanone S,S-dioxide
72) (±)-Trans-1-(3-Ethyl-2,3,4,5-tetrahydro-9-methoxy-5-phenyl-1,4-benzothiazepin-3-yl)-2-butanone S,S-dioxide
73) (±)-Trans-3-((3-ethyl-2,3,4,5-tetrahydro-3-(2-oxobutyl)-5-phenyl-1,4-benzothiazepin-7-yl)oxy)propanesulfonic acid 1,1-dioxide
74) (±)-Trans-1-(3-Ethyl-2,3,4,5-tetrahydro-7,8-diethoxy-5-phenyl-1,4-benzothiazepin-3-yl)-2-butanone S,S-dioxide
75) (±)-Trans-1-(3-Ethyl-2,3,4,5-tetrahydro-7,8-dimethoxy-4-hydroxy-5-phenyl-1,4-benzothiazepin-3-yl)-2-butanone S,S-dioxide
76) (±)-Trans-3-((3-ethyl-2,3,4,5-tetrahydro-3-(2-oxobutyl)-5-phenyl-1,4-benzothiazepin-8-yl)oxy)propanesulfonic acid 1,1-dioxide
77) (±)-Trans-2-((3-ethyl-2,3,4,5-tetrahydro-3-(2-oxobutyl)-5-phenyl-1,4-benzothiazepin-7-yl)oxy)ethyltrimethylammnonium iodide 1,1-dioxide
78) (±)-Trans-2-((3-ethyl-2,3,4,5-tetrahydro-3-(2-oxobutyl)-5-phenyl-1,4-benzothiazepin-8-yl)oxy)ethyltrimethylammonium iodide 1,1-dioxide Pharmaceutical Composition Examples In the following Examples, the active compound can be any compound of formula (I) and/or a pharmaceutically acceptable salt, solvate, or physiologically functional derivative thereof. The active compound is preferably 3-methyl-3-isopropyl-2,3,4,5-tetrahydro-5-phenyl-1,4-benzothiazepine 1,1-dioxide or one of the compounds of Synthetic Examples 2 to 30.

(i) Tablet compositions

The following compositions A and B can be prepared by wet granulation of ingredients (a) to (c) and (a) to (d) with a solution of povidone, followed by addition of the magnesium stearate and compression.

Composition A

|  | mg/tablet | mg/tablet |
| --- | --- | --- |
| (a) Active ingredient | 250 | 250 |
| (b) Lactose B.P. | 210 | 26 |
| (c) Sodium Starch Glycollate | 20 | 12 |
| (d) Povidone B.P. | 15 | 9 |
| (e) Magnesium Stearate | 5 | 3 |
|  | 500 | 300 |

Composition B

|  | mg/tablet | mg/tablet |
| --- | --- | --- |
| (a) Active ingredient | 250 | 250 |
| (b) Lactose 150 | 150 | — |
| (c) Avicel PH 101 | 60 | 26 |
| (d) Sodium Starch Glycollate | 20 | 12 |
| (e) Povidone B.P. | 15 | 9 |
| (f) Magnesium Stearate | 5 | 3 |
|  | 500 | 300 |

Composition C

|  | mg/tablet |
| --- | --- |
| Active ingredient | 100 |
| Lactose | 200 |
| Starch | 50 |
| Povidone | 5 |
| Magnesium Stearate | 4 |
|  | 359 |

The following compositions D and E can be prepared by direct compression of the admixed ingredients. The lactose used in formulation E is of the direct compression type.

Composition D

|  | mg/tablet |
| --- | --- |
| Active ingredient | 250 |
| Magnesium Stearate | 4 |
| Pregelatinised Starch NF15 | 146 |
|  | 400 |

Composition E

|  | mg/tablet |
| --- | --- |
| Active ingredient | 250 |
| Magnesium Stearate | 5 |
| Lactose | 145 |
| Avicel | 100 |
|  | 500 |

Composition F (Controlled release composition)

|  | mg/tablet |
| --- | --- |
| (a) Active ingredient | 500 |
| (b) Hydroxypropylmethylcellulose (Methocel K4M Premium) | 112 |
| (c) Lactose B.P. | 53 |
| (d) Povidone B.P.C. | 28 |
| (e) Magnesium Stearate | 7 |
|  | 700 |

The composition can be prepared by wet granulation of ingredients (a) to (c) with a solution of povidone, followed by addition of the magnesium stearate and compression.

Composition G (Enteric-coated tablet)

Enteric-coated tablets of Composition C can be prepared by coating the tablets with 25 mg/tablet of an enteric polymer such as cellulose acetate phthalate, polyvinylacetate phthalate, hydroxypropylmethyl-cellulose phthalate, or anionic polymers of methacrylic acid and methacrylic acid methyl ester (Eudragit L). Except for Eudragit L, these polymers should also include 10% (by weight of the quantity of polymer used) of a plasticizer to prevent membrane cracking during application or on storage. Suitable plasticizers include diethyl phthalate, tributyl citrate and triacetin.

Composition H (Enteric-coated controlled release tablet)

Enteric-coated tablets of Composition F can be prepared by coating the tablets with 50 mg/tablet of an enteric polymer such as cellulose acetate phthalate. polyvinylacetate phthalate, hydroxypropylmethyl-cellulose phthalate, or anionic polymers of methacrylic acid and methacrylic acid methyl ester (Eudgragit L). Except for Eudgragit L, these polymers should also include 10% (by weight of the quantity of polymer used) of a plasticizer to prevent membrane cracking during application or on storage. Suitable plasticizers include diethyl phthalate, tributyl citrate and triacetin.

(ii) Capsule compositions

Composition A

Capsules can be prepared by admixing the ingredients of Composition D above and filling two-part hard gelatin capsules with the resulting mixture. Composition B (infra) may be prepared in a similar manner.

Composition B

|  | mg/capsule |
| --- | --- |
| (a) Active ingredient | 250 |
| (b) Lactose B.P. | 143 |
| (c) Sodium Starch Glycollate | 25 |
| (d) Magnesium Stearate | 2 |
|  | 420 |

Composition C

|  | mg/capsule |
| --- | --- |
| (a) Active ingredient | 250 |
| (b) Macrogol 4000 BP | 350 |
|  | 600 |

Capsules can be prepared by melting the Macrogol 4000 BP, dispersing the active ingredient in the melt and filling two-part hard gelatin capsules therewith.

Composition D

|  | mg/capsule |
| --- | --- |
| Active ingredient | 250 |
| Lecithin | 100 |
| Arachis Oil | 100 |
|  | 450 |

Capsules can be prepared by dispersing the active ingredient in the lecithin and arachis oil and filling soft, elastic gelatin capsules with the dispersion.

Composition E (Controlled release capsule)

|  | mg/capsule |
| --- | --- |
| (a) Active ingredient | 250 |
| (b) Microcrystalline Cellulose | 125 |
| (c) Lactose BP | 125 |
| (d) Ethyl Cellulose | 13 |
|  | 513 |

The controlled release capsule formulation can be prepared by extruding mixed ingredients (a) to (c) using an extruder, then spheronising and drying the extrudate. The dried pellets are coated with a release controlling membrane (d) and filled into two-part, hard gelatin capsules.

Composition F (Enteric capsule)

|  | mg/capsule |
| --- | --- |
| (a) Active ingredient | 250 |
| (b) Microcrystalline Cellulose | 125 |
| (c) Lactose BP | 125 |
| (d) Cellulose Acetate Phthalate | 50 |
| (e) Diethyl Phthalat | 5 |
|  | 555 |

The enteric capsule composition can be prepared by extruding mixed ingredients (a) to (c) using an extruder, then spheronising and drying the extrudate. The dried pellets are coated with an enteric membrane (d) containing a plasticizer (e) and filled into two-part, hard gelatin capsules.

Composition G (Enteric-coated controlled release capsule)

Enteric capsules of Composition E can be prepared by coating the controlled-release pellets with 50 mg/capsule of an enteric polymer such as cellulose acetate phthalate, polyvinylacetate phthalate, hydroxypropylmethylcellulose phthalate, or anionic polymers of methacrylic acid and methacrylic acid methyl ester (Eudragit L). Except for Eudragit L, these polymers should also include 10% (by weight of the quantity of polymer used) or a plasticizer to prevent membrane cracking during application or on storage. Suitable plasticizers include diethyl phthalate, tributyl citrate and triacetin.

(iii) Intravenous injection composition

| Active ingredient | 0.200 g |
| --- | --- |
| Sterile, pyrogen-free phosphate buffer (pH 9.0) to | 10 ml |

The active ingredient is dissolved in most of the phosphate buffer at 35°–40° C., then made up to volume and filtered through a sterile micropore filter into sterile 10 ml glass vials (Type 1) which are sealed with sterile closures and overseals.

(iv) Intramuscular injection composition

| Active ingredient | 0.20 g |
| --- | --- |
| Benzyl Alcohol | 0.10 g |
| Glycofurol 75 | 1.45 g |
| Water for Injection q.s. to | 3.00 ml |

The active ingredient is dissolved in the glycofurol. The benzyl alcohol is then added and dissolved, and water added to 3 ml. The mixture is then filtered through a sterile micropore filter and sealed in sterile 3 ml glass vials (Type 1).

(v) Syrup composition

| Active ingredient | 0.25 g |
| --- | --- |
| Sorbitol Solution | 1.50 g |
| Glycerol | 1.00 g |
| Sodium Benzoate | 0.005 g |
| Flavour | 0.0125 ml |
| Purified Water q.s. to | 5.0 ml |

The sodium benzoate is dissolved in a portion of the purified water and the sorbitol solution added. The active ingredient is added and dissolved. The resulting solution is mixed with the glycerol and then made up to the required volume with the purified water.

(vi) Suppository composition

|  | mg/suppository |
| --- | --- |
| Active ingredient | 250 |
| Hard Fat BP (Witepsol H15 - Dynamit NoBel) | 1770 |
|  | 2020 |

One-fifth of the Witepsol H15 is melted in a steam-jacketed pan at 45° C. maximum. The active ingredient is sifted through a 200 ml sieve and added to the molten base with mixing, using a Silverson fitted with a cutting head, until a smooth dispersion is achieved. Maintaining the mixture at 45° C., the remaining Witepsol H15 is added to the suspension which is stirred to ensure a homogenous mix. The entire suspension is then passed through a 250 ml stainless steel screen and, with continuous stirring, allowed to cool to 40° C. At a temperature of 38°–40° C. 2.02 g aliquots of the mixture are filled into suitable plastic moulds and the suppositories allowed to cool to room temperature.

(vii) Pessary composition

|  | mg/pessary |
| --- | --- |
| Active ingredient (631 m) | 250 |
| Anhydrous Dextrose | 380 |
| Potato Starch | 363 |
| Magnesium Stearate | 7 |
|  | 1000 |

The above ingredients are mixed directly and pessaries prepared by compression of the resulting mixture.

(viii) Transdermal composition

| Active ingredient | 200 mg |
| --- | --- |
| Alcohol USP | 0.1 ml |
| Hydroxyethyl cellulose |  |

The active ingredient and alcohol USP are gelled with hydroxyethyl cellulose and packed in a transdermal device with a surface area of 10 cm$^2$.

Biological Assay

In vitro inhibition of bile acid uptake

Freshly prepared rat distal ileal brush border membrane vesicles (about 200 mg vesicle protein) were incubated for 30 seconds at 24° C. in an incubation mixture comprising 101M $^3$H taurocholate, 100 mM NaCl (or KCl) and 80 mM mannitol in 20 mM Herpes Tris pH 7.4. Each test compound was dissolved in ethanol (or water) and then diluted with incubation mixture to an ethanol concentration of not more than 1% v/v. The incubation was terminated by rapid dilution and filtration and the filter washed with an ice-cold isotonic sodium-free buffer.

The uptake of $^3$H taurocholate was measured by the radioactivity remaining on the filter and converted to pmoles/mg vesicle protein. The active, ie sodium-dependent, uptake was obtained by subtracting the passive uptake measured in 100 mM KCl from the total uptake measured in 100 mM NaCl. The active uptake for each test compound was compared with a control active uptake and the results expressed as % inhibition of bile acid uptake.

Below is given data for compounds of the invention showing % inhibition of bile acid uptake at various concentrations of compound.

| Example | 10 μM | 3 μM | 1 μM | 0.3 μM |
|---|---|---|---|---|
| 5 | 98 | 94 | 83 | 60 |
| 3 | 95 | 86 | 67 | 38 |
| 51 | 100 | 100 | 91 | 66 |
| 4 | 90 | 77 | 54 | 28 |
| 12 | 87 | 64 | 44 | 28 |
| 2 | 77 | 64 | 39 | 11 |
| 7 | 53 | | | |
| 10 | 69 | | | |
| 11 | 64 | 36 | 33 | 15 |
| 42 | 42 | | | |
| 39 | 14 | | | |
| 20 | 27 | | | |

We claim:

1. A compound of formula (Ia):

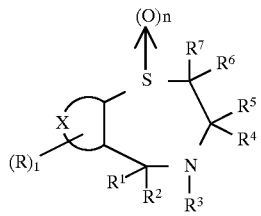

wherein:

$l$ is an integer of from 0 to 4;

$n$ is an integer of from 0 to 2;

R is an atom or group selected from halogen, cyano, nitro, alkyl, alkoxy, aryl, pyrryl, thienyl, pyridyl, aryloxy, arylalkoxy, aralkyl, alkaryl, $-O(CH_2)_pSO_3R^{11}$, $-O(CH_2)_pNR^{11}R^{12}$, $-O(CH_2)_pN^+R^{11}R^{12}R^{14}$, $COR^{11}$, $-CO_2R^{11}$, $-CONR^{11}R^{12}$, $-CH_2OR^{11}$, $-NR^{11}R^{12}$, $-NHCOR^{11}$, $-NHSO_2R^{11}$, $-SR^{11}$, $-SO_2R^{11}$, $-SO_2NR^{11}R^{12}$, $-SO_3R^{11}$, wherein p is an integer from 1 to 4, $R^{11}$ and $R^{12}$ are independently selected from hydrogen, $C_{1-6}$ alkyl and phenyl, and $R^{14}$ is hydrogen or $C_{1-6}$ alkyl, or R is a group $-OCH_2O-$ which forms a further ring attached to X, wherein said alkyl, alkoxy, aryl, pyrryl, thienyl, pyridyl, aryloxy, arylalkoxy, aralkyl and alkaryl groups are optionally substituted by one or more atoms or groups selected from halogen, nitro, nitrile, alkyl, alkoxy, $-COR^{11}$, $-CO_2R^{11}$, $-SO_3R^{11}$ wherein $R^{11}$ is as hereinbefore defined and $-NR^{14}R^{15}$ wherein $R^{14}$ is as hereinbefore defined and $R^{15}$ is hydrogen or $C_{1-6}$ alkyl;

$R^1$ is hydrogen or $C_{1-6}$ alkyl;

$R^2$ is an atom or group selected from hydrogen, $C_{1-6}$ alkyl, $C_{1-4}$ alkoxy, pyrryl, thienyl, pyridyl, 1,3-benzodioxolo, phenyl and naphthyl, which groups are optionally substituted by one or more atoms or groups independently selected from halogen, cyano, nitro, carboxyl, phenyl, phenoxy, benzyloxy, $-COR^{11}$, $-CO_2R^{11}$, $-CONR^{11}R^{12}$, $-CH_2OR^{11}$, $-NR^{11}R^{12}$, $-NHCOR^{11}$, $-NHSO_2R^{11}$, $-SR^{11}$, $-SO_2R^{11}$, $-SO_3R^{11}$ (wherein $R^{11}$ and $R^{12}$ are as hereinbefore defined), $-O(CH_2)_pNR^{11}R^{12}$, $-O(CH_2)_pN^+R^{11}R^{12}R^{13}$ and $-O(CH_2)_pSO_3R^{11}$ (wherein p, $R^{11}$ and $R^{12}$ are as hereinbefore defined and $R^{13}$ is hydrogen or $C_{1-6}$ alkyl);

$R^3$ is hydrogen, OH, $C_{1-6}$ alkyl, $C_{1-6}$ alkoxy or $-O C_{1-6}$ acyl;

$R^4$ is a group independently selected from $C_{1-6}$ alkyl (including cycloalkyl and cycloalkylalkyl), $C_{2-6}$ alkenyl and $C_{2-6}$ alkynyl, which groups are optionally substituted by one or more atoms or groups independently selected from halogen, oxo, $C_{1-4}$ alkoxy, $-CO_2R^{14}$, $-NR^{14}R^{15}$, $-SR^{14}$, $-S(O)C_{1-6}$ alkyl, $-SO_2R^{14}$, $-SO_3R^{14}$ (wherein $R^{14}$ and $R^{15}$ are hereinbefore defined);

$R^5$ is a group independently selected from $C_{2-6}$ alkyl (including cycloalkyl and cycloalkylalkyl), $C_{2-6}$ alkenyl, and $C_{2-6}$ alkynyl, which groups are optionally substituted by one or more atoms or groups independently selected from halogen, oxo, $C_{1-4}$ alkoxy, $-CO_2R^{14}$, $-NR^{14}R^{15}$, $-SR^{14}$, $-S(O) C_{1-6}$ alkyl, $-SO_2R^{14}$, $-SO_3R^{14}$ (wherein $R^{14}$ and $R^{15}$ are hereinbefore defined);

or $R^4$ and $R^5$, together with the carbon atom to which they are attached, form a $C_{3-7}$ spiro cycloalkyl group which is optionally substituted by one or more atoms or groups independently selected from halogen, $C_{1-6}$ alkoxy, $-CO_2R^{14}$, $-SO_3R^{14}$ and $-NR^{14}R^{15}$ (where $R^{14}$ and $R^{15}$ are as hereinbefore defined);

$R^6$ and $R^7$ are independently selected from hydrogen and $C_{1-6}$ alkyl; and X is a fused phenyl ring;

with the proviso that when l is an integer of from 0 to 4, $R^1=R^6=R^7=H$, $R^3=H$ or OH, $R^2=$ unsubstituted phenyl or phenyl substituted by one or more atoms or groups independently selected from halogen, nitro, phenylalkoxy, $C_{1-4}$ alkoxy, $C_{1-6}$ allyl and $-O(CH_2)_p SO_3R^{11}$ wherein p and $R^{11}$ are as hereinbefore defined, wherein said phenylalkoxy, alkoxy and alkyl groups are optionally substituted by one or more halogen atoms, then $R^4$ is other than a $C_{1-6}$ straight alkyl group and $R^5$ is other than a $C_{2-5}$ straight alkyl group, and salts, solvates and physiologically functional derivatives thereof.

2. A compound as claimed in claim 1 which is a trans isomer wherein:

$l$ is 0, 1 or 2;

$n$ is 1 or 2;

$R^1$, $R^6$ and $R^7$ are all hydrogen;

$R^3$ is hydrogen; and

X is a fused phenyl, naphthyl, pyrryl, thienyl or pyridyl, group.

3. A compound as claimed in claim 2 wherein $l$ is 0 or 1;

$n$ is 2; and $R^2$ is pyrryl, thienyl, pyridyl, phenyl or naphthyl, such groups being optionally substituted by one or more atoms or groups independently selected from halogen, cyano, nitro, carboxyl, phenyl, phenoxy, benzyloxy, $-COR^{11}$, $-CO_2R^{11}$, $-CONR^{11}R^{12}$, $-CH_2OR^{11}$, $-NR^{11}R^{12}$, $-NHCOR^{11}$, $-NHSO_2R^{11}$, $-SR^{11}$, $-SO_2R^{11}$, $-SO_3R^{11}$ (wherein $R^{11}$ and $R^{12}$ are independently selected from hydrogen, $C_{1-6}$ alkyl and phenyl), $-O(CH_2)_pNR^{11}R^{12}$, $-O(CH_2)_pN^+R^{11}R^{12}R^{13}$ and $-O(CH_2)_pSO_3R^{11}$ (wherein p is an integer of from 1 to 4, $R^{11}$ and $R^{12}$ are as hereinbefore defined and $R^{13}$ is hydrogen or $C_{1-6}$ alkyl).

4. A compound as claimed in claim 1 which is:

2,3,4,5-Tetrahydro-5-phenylspiro(1,4-benzothiazepine-3,1'-cyclohexane) 1,1-dioxide;

(±)-Trans-2,3,4,5-tetrahydro-3-isopropyl-3-methyl-5-phenyl-1,4-benzothiazepine 1,1-dioxide;

(+)-(S)-2,3,4,5-Tetrahydro-5-phenylspiro(1,4-benzothiazepine-3,1'-cyclohexane) 1,1-dioxide;

(−)-(R)-2,3,4,5-Tetrahydro-5-phenylspiro(1,4-benzothiazepine-3,1'-cyclohexane) 1,1-dioxide;

2,3,4,5-Tetrahydro-3-isopropyl-3-methyl-5-phenyl-1,4-benzothiazepine hydrochloride;
3-sec-Butyl-2,3,4,5-tetrahydro-3-methyl-5-phenyl-1,4-benzothiazepine hydrochloride;
4,5-Dihydro-5-phenylspiro(1,4-benzothiazepine-3-(2H), 1'-cyclopentane)hydrochloride;
2,3,4,5-Tetrahydro-5-phenylspiro(1,4-benzothiazepine-3,1'-cyclohexane)hydrochloride;
5-(2-Fluorophenyl)-2,3,4,5-tetrahydrospiro(1,4-benzothiazepine-3,1'-cyclohexane) 1,1-dioxide;
(±)-Cis-3-(2,3,4,5-tetrahydro-3-methyl-5-phenyl-1,4-benzothiazepin-3-yl)propionic acid 1,1-dioxide;
(±)-Trans-ethyl 3-(2,3,4,5-tetrahydro-3-methyl-5-phenyl-1,4-benzothiazepin-3-yl)propionate 1,1-dioxide;
(±)-Trans-ethyl 3-(3-ethyl-2,3,4,5-tetrahydro-5-phenyl-1,4-benzothiazepin-3-yl)propionate 1,1-dioxide;
(±)-Cis-ethyl 5-(2,3,4,5-tetrahydro-3-methyl-5-phenyl-1,4-benzothiazepin-3-yl)valerate 1,1-dioxide;
(±)-Trans-3-((E)-2-butenyl)-3-ethyl-2,3,4,5-tetrahydro-5-phenyl-1,4-benzothiazepine;
(±)-Trans-3-((E)-2-butenyl)-3-ethyl-2,3,4,5-tetrahydro-5-phenyl-1,4-benzothiazepine 1,1-dioxide;
(±)-Cis-3-ethyl-2,3,4,5-tetrahydro-3-isopropyl-5-phenyl-1,4-benzothiazepine 1,1-dioxide;
(±)-Trans-3-ethyl-2,3,4,5-tetrahydro-3-isopropyl-5-phenyl-1,4-benzothiazepine 1,1-dioxide;
(±)-Cis-3-iso-butyl-3-ethyl-2,3,4,5-tetrahydro-5-phenyl-1,4-benzothiazepine 1-oxide;
(±)-Cis-3-iso-butyl-3-ethyl-2,3,4,5-tetrahydro-5-phenyl-1,4-benzothiazepine 1,1-dioxide;
(±)-Trans-3-iso-butyl-3-ethyl-2,3,4,5-tetrahydro-5-phenyl-1,4-benzothiazepine 1-oxide;
(±)-Trans-3-iso-butyl-3-ethyl-2,3,4,5-tetrahydro-5-phenyl-1,4-benzothiazepine 1,1-dioxide;
(±)-Cis-3-butyl-3-ethyl-2,3,4,5-tetrahydro-5-(3-pyridyl)-1,4-benzothiazepine 1,1-dioxide;
(±)-Trans-3-butyl-3-ethyl-2,3,4,5-tetrahydro-5-(3-pyridyl)-1,4-benzothiazepine 1,1-dioxide;
(±)-Trans-3-(3-methoxypropyl)-3-ethyl-2,3,4,5-tetrahydro-5-phenyl-1,4-benzothiazepine 1,1-dioxide; or
(±)-Cis-3-ethyl-2,3,4,5-tetrahydro-5-phenyl-1,4-benzothiazepine-3-carbaldehyde 1,1-dioxide.

5. A compound of claim 1 which is:
(±)-Trans-2,3,4,5-tetrahydro-3-isopropyl-3-methyl-5-phenyl-1,4-benzothiazepine 1,1-dioxide;
(±)-Trans-3-((E)-2-butenyl)-3-ethyl-2,3,4,5-tetrahydro-5-phenyl-1,4-benzothiazepine 1,1-dioxide;
(±)-Cis-3-ethyl-2,3,4,5-tetrahydro-3-isopropyl-5-phenyl-1,4-benzothiazepine 1,1-dioxide; or
(±)-Trans-3-ethyl-2,3,4,5-tetrahydro-3-isopropyl-5-phenyl-1,4-benzothiazepine 1,1-dioxide.

6. A process for the preparation of the compound of formula (Ia) as claimed in claim 1, wherein n=0 and $R^1$ and $R^3$ are hydrogen, which comprises at least the step of reducing the imine bond of a compound of formula (II) with a metal hydride:

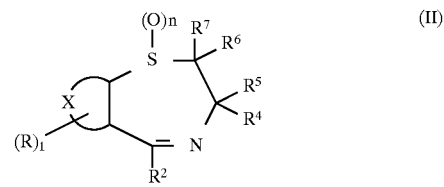

wherein l, R, $R^2$, $R^4$ to $R^7$ and X are as defined for the compound of formula (Ia) and wherein n=0.

7. A pharmaceutical composition comprising the compound as claimed in claims 1, 2, 3, 4, or 5 together with one or more pharmaceutically acceptable carriers.

8. A method of treating a hyperlipidemic condition in a mammal comprising administering to the mammal an effective treatment amount of the pharmaceutical composition of claim 7.

9. A method according to claim 8 wherein the mammal is a human.

* * * * *